(12) United States Patent
Simpson, III et al.

(10) Patent No.: US 7,542,143 B2
(45) Date of Patent: *Jun. 2, 2009

(54) LIQUID MEASUREMENT CELL HAVING A PRESSURIZED AIR CAVITY THEREIN

(75) Inventors: Thomas W. Simpson, III, Boothwyn, PA (US); Anthony Joseph Martino, West Chester, PA (US); Ken Stephen Schermacher, Chadds Ford, PA (US); Matthew Paul Reinhardt, Richmond, VA (US); Jeff B. Alspach, Lake Orion, MI (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 125 days.

This patent is subject to a terminal disclaimer.

(21) Appl. No.: 11/634,581

(22) Filed: Dec. 5, 2006

(65) Prior Publication Data

US 2007/0131018 A1 Jun. 14, 2007

Related U.S. Application Data

(60) Provisional application No. 60/742,455, filed on Dec. 5, 2005.

(51) Int. Cl.
*G01N 21/00* (2006.01)
*G01N 1/10* (2006.01)
(52) U.S. Cl. .................................. 356/436; 356/246
(58) Field of Classification Search .................. 356/436
See application file for complete search history.

(56) References Cited

U.S. PATENT DOCUMENTS

| | | |
|---|---|---|
| 3,628,867 A | 12/1971 | Brady |
| 3,690,771 A | 9/1972 | Armstrong et al. |
| 4,403,866 A | 9/1983 | Falcoff et al. |
| 4,479,718 A | 10/1984 | Alman |
| 4,511,251 A | 4/1985 | Falcoff et al. |

(Continued)

FOREIGN PATENT DOCUMENTS

| | | |
|---|---|---|
| DE | 25 25 701 A1 | 12/1976 |
| DE | 100 50 416 | 4/2002 |
| DE | 103 52 924 | 7/2005 |
| EP | 584654 | 3/1994 |
| GB | 1589705 | 5/1981 |

(Continued)

OTHER PUBLICATIONS

Yang et al. "a-Cyclodextrin . . . " Analytica Acta 537 (2005) 385-392.
Yokoyama "Simple System . . . " Review of Scientific Instr., 64 (1993) 1369-70.

*Primary Examiner*—Tarifur Chowdhury
*Assistant Examiner*—Tara S Pajoohi

(57) ABSTRACT

A flow cell for measuring the color properties of a liquid flowing therethrough using interrogating radiation at a predetermined wavelength has a thin partition mounted in spaced relationship between both a window and a base of the cell. The partition and the window define an air cavity therebetween. The spacing between the partition and the window is such that evanescent coupling of radiation reflected from the liquid into the material of the window is prevented.

The cell has a pressurized fluid inflow channel and a pressurized fluid outflow channel formed therein. Each of the inflow and outflow channels communicates with the air cavity. The inflow and outflow channels are sized to pass a pressurized fluid, such as pressurized air, through the air cavity such that, in use, the spaced relationship between the partition and the window is maintained by pressurized fluid in the air cavity. The pressure of the pressurized fluid in the air cavity is determined in accordance with the pressure of the liquid flowing through the cell.

10 Claims, 14 Drawing Sheets

U.S. PATENT DOCUMENTS

| | | | |
|---|---|---|---|
| 4,652,745 A | 3/1987 | Zanardelli | |
| 4,707,134 A | 11/1987 | McLachlan et al. | |
| 4,714,345 A | 12/1987 | Schrader | |
| 4,816,670 A | 3/1989 | Kitamura et al. | |
| 4,867,559 A | 9/1989 | Bach | |
| 4,887,217 A | 12/1989 | Sherman et al. | |
| 4,936,685 A | 6/1990 | Taylor et al. | |
| 5,194,915 A | 3/1993 | Gilby | |
| 5,223,142 A | 6/1993 | Kollbert | |
| 5,777,726 A | 7/1998 | Krone-Schmidt | |
| 5,811,793 A | 9/1998 | Pientka | |
| 5,963,332 A | 10/1999 | Feldmann et al. | |
| 6,032,341 A | 3/2000 | Cain et al. | |
| 6,188,474 B1 | 2/2001 | Dussault et al. | |
| 6,223,142 B1 | 4/2001 | Bargh et al. | |
| 6,288,783 B1 | 9/2001 | Auad | |
| 6,292,264 B1 | 9/2001 | Voye et al. | |
| 6,535,283 B1 | 3/2003 | Heffels et al. | |
| 6,583,878 B2 | 6/2003 | Hustert | |
| 6,867,861 B2 | 3/2005 | Martino et al. | |
| 2002/0149773 A1* | 10/2002 | Martino et al. | 356/436 |
| 2004/0190367 A1 | 9/2004 | Wierzbicki et al. | |
| 2005/0174561 A1 | 8/2005 | Murakami et al. | |
| 2005/0266582 A1 | 12/2005 | Modlin et al. | |
| 2006/0043301 A1 | 3/2006 | Mantele et al. | |

FOREIGN PATENT DOCUMENTS

| | | |
|---|---|---|
| GB | 2228083 | 8/1990 |
| JP | 2000 193586 | 7/2000 |
| WO | WO 99/41003 | 8/1999 |
| WO | WO 99/48602 | 9/1999 |
| WO | WO 01/63248 | 8/2001 |
| WO | WO 2005/062022 | 7/2005 |

\* cited by examiner

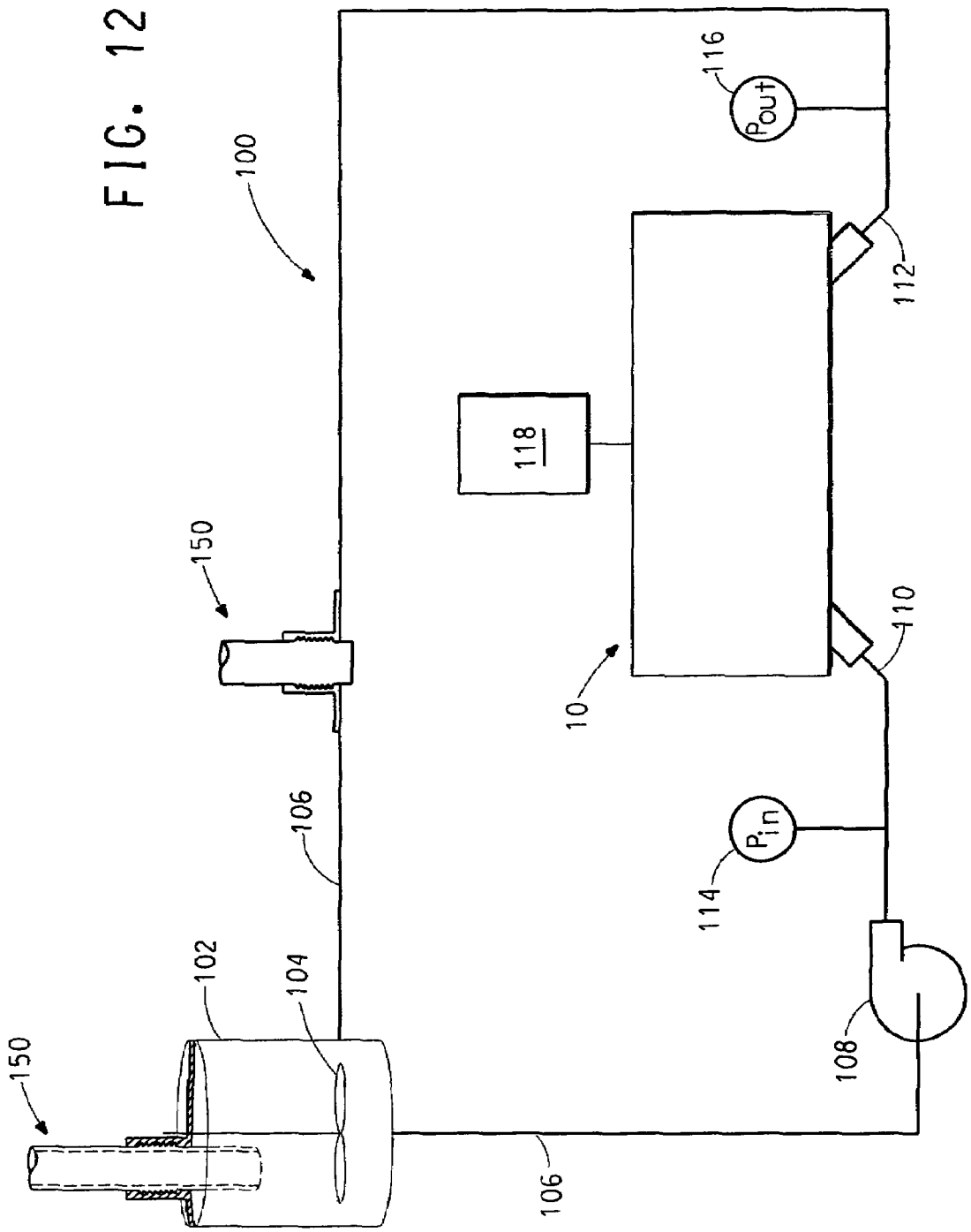

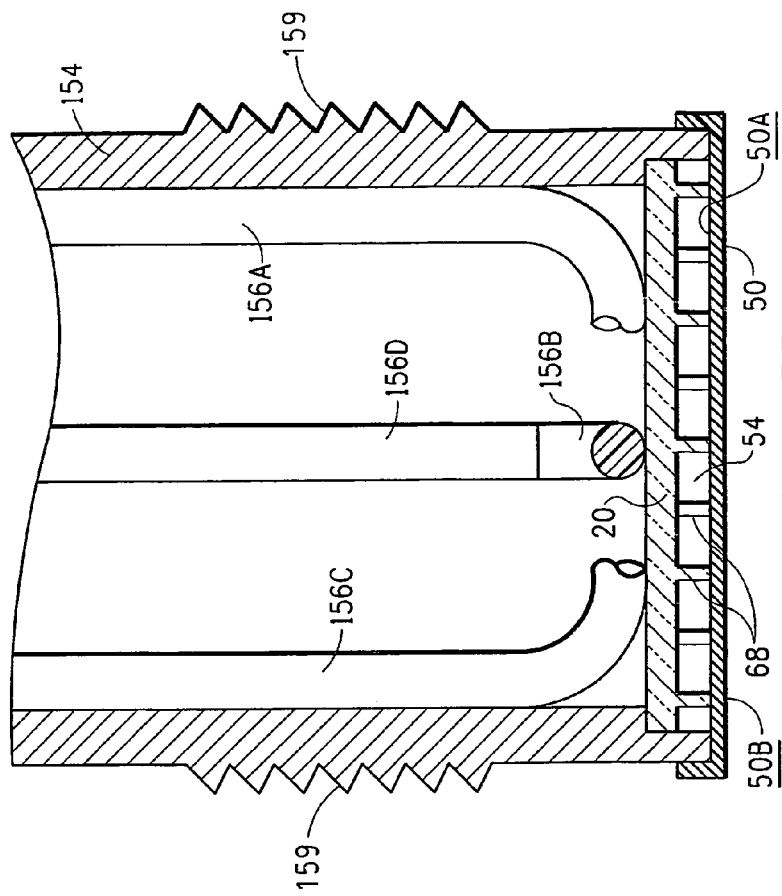
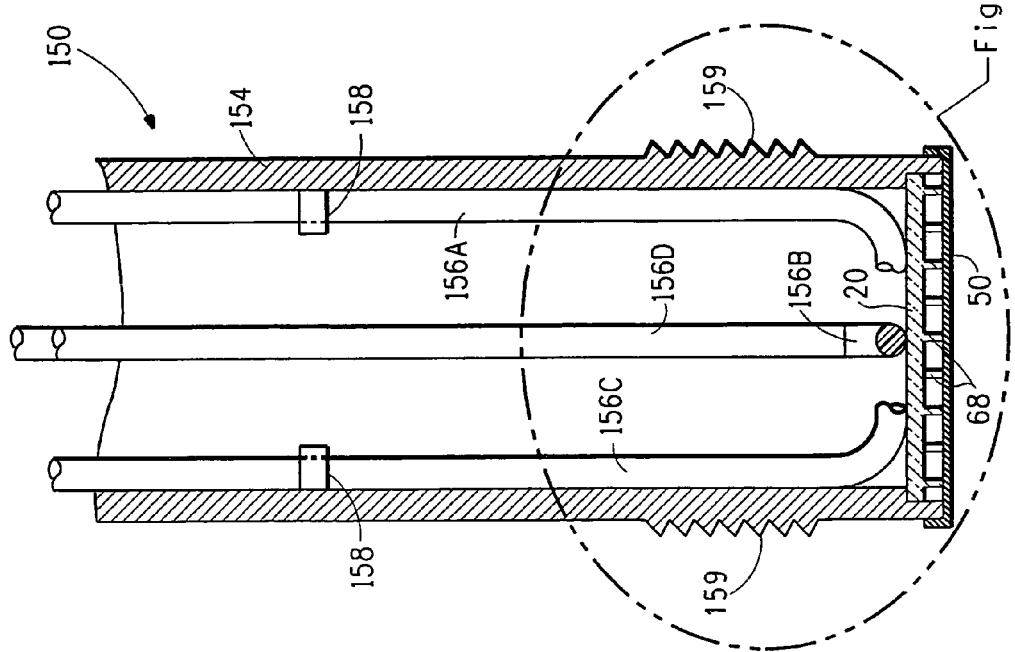

LIQUID MEASUREMENT CELL HAVING A PRESSURIZED AIR CAVITY THEREIN

CROSS REFERENCE TO RELATED APPLICATIONS

This application claims the benefit of U.S. Provisional Application; 60/742,455 which was filed 5 Dec. 2005, and is incorporated as a part hereof for all purposes.

Subject matter disclosed herein is disclosed and claimed in the following copending applications, all filed contemporaneously herewith and all assigned to the assignee of the present invention:

Liquid Measurement Cell Having A Transparent Partition Therein (FA-1187);

System for Measuring A Color Property Of A Liquid (FA-1320);

Probe Apparatus For Measuring A Color Property Of A Liquid (FA-1506); and

Method For Measuring A Color Property Of A Liquid (FA-1507).

BACKGROUND OF THE INVENTION

1. Field of the Invention

This invention relates to a flow cell for measuring the color properties of a liquid, such as paint, that utilizes a pressuring fluid to space a partition from a window of a flow cell.

2. Description of the Art

Pigment dispersions and tints are widely used in formulating high performance liquid coating compositions. Such compositions are used, for example, as exterior finish paints for automobiles and trucks.

Dry color measurement of such liquid compositions is believed to be the most accurate indication of the composition's color properties. Such measurement is usually made manually by taking an aliquot of the composition being prepared. The composition is sprayed as a coating onto a panel and the panel is baked and dried. One or more color properties of the dried coating may be measured against a reference using a colorimeter or spectrophotometer. Based upon the measurement the batch under preparation is adjusted in an effort to obtain a closer match to the reference. Manual color measurements are very time consuming, primarily due to the long preparation and drying times. Also, the procedure may have to be repeated numerous times before the desired color property is achieved.

It is believed that manufacturing efficiencies may be achieved through the ability to measure the color properties of a liquid composition while in a wet state. However, to be effective, any wet color measurement must accurately predict the color of the composition when dried. This goal has proved elusive.

Instruments employing a reflectance spectrophotometer have been used to obtain a free surface reflectance measurement of a wet liquid dispersion. Representative of these instruments are the devices described in U.S. Pat. No. 6,583,878 (Hustert), U.S. Pat. No. 6,292,264 (Voye et al.) and German Patent DE 25 25 701 (Langer). These instruments all employ a free surface reflectance measurement of a wet coating film utilizing a spectrophotometer. The measurements taken from these instruments thus embody the best representation of the color of the coating film that could be correlated with the measurements of the same film in its dry state. However, surface non-uniformities of such wet coatings, as well as viscosity variations, settling, and flocculation could still lead to erroneous results and unacceptable measurement variability.

It is believed that further efficiencies can be achieved by coupling such a device to a manufacturing process. However, coupling such devices as just described to a continuous process has its own encumbering difficulties, including but not limited to, operation of said device in the presence of volatile flammable solvents emitted from the sample surface as well as cleaning.

To couple a color measurement device to a manufacturing process, in light of the aforementioned possible presence of volatile flammable solvents, as well as taking into consideration that many processes operate at super-ambient pressures, it is standard practice to contain the fluid sample flow through the device in a closed system, separated from the illumination source and spectral detector by a window of sufficient strength, and therefore thickness, to withstand said pressure. The thickness T required of such a window is given by the equation:

$$T = \sqrt{\frac{zPD'^2}{\sigma}}$$

where z is a shape factor for the window;

P is the pressure being contained;

D' is the unsupported diameter, and

σ is the maximum design stress (pressure) for the window material.

Instruments which measure the absorbance and/or scattering properties of a liquid contained in a closed system have been proposed for standard spectrophotometric measurements, including both laboratory and process applications, either in transmission or reflectance mode. Some of these instruments also purport to measure the color of the liquid in reflectance mode through a sight glass into the process stream or within a sample cell employing a window between the sample and the detector. U.S. Pat. No. 4,511,251 (Falcoff et al.) and U.S. Pat. No. 6,288,783 (Auad et al.) are representative of this class of instrument.

The instrument described in the last referenced patent employs a variable pathlength measurement cell to measure properties of liquids, including color. The instrument employs a closed path for the flow of the liquid to be measured, thus allowing it to be placed in hazardous classification areas within a manufacturing plant environment. However, this particular instrument has multiple moving parts which are part of the liquid path, which can cause difficulty in cleaning, and are difficult to maintain. Another disadvantage is that the instrument requires high volumes of liquid sample to take proper readings. Moreover, while the instrument can measure in both reflectance and transmission modes, it employs 0/0 geometry for each. As a result, in transmission mode no information is provided about scattered light from the fluid being analyzed. In reflection mode unmitigated backscattered light from the source washes out the color sensitivity.

Ultimately, the single most significant issue to overcome in the measurement of the color of a liquid in intimate contact with the window of the flow cell is the disruption of light on its way back to the detector that occurs because of the presence of the window itself. Causes of such disruption of the light include, but are not limited to, reflection, refraction, total internal reflection, and loss or escape of said light with reference to the various surfaces of the window. As a result of such disruption the light ultimately either never reaches the detector or is modified by the surfaces of the window with which it interacts, such that spectral information presented to the detector is no longer truly representative of the sample being measured.

A liquid in intimate contact with a viewing window looks different to the human eye when viewed through that window than the color of the same liquid when viewed in a free surface fashion, i.e., with nothing between the eye and the free surface of the wet liquid.

FIG. 1 is a stylized diagrammatic representation of the optical phenomena occurring at the interface between a liquid L and a window W. The window W may form part of a flow cell or a probe. The liquid L is flowing past the window in a flow direction G at some predetermined fluid pressure. The liquid L is in contact with the window W. The light scattering pigments of the liquid composition are usually dispersed in a solvent vehicle that has an index of refraction close to the index of refraction of the window material.

To gain a better understanding of the optical effects that occur when a liquid is viewed through a window, consider the situation depicted in FIG. 1. As a light ray R propagates through a medium M (e.g., air) it impinges upon the exterior surface E of the window W. The material of the window W refracts the ray R. The refracted ray R' propagates through the window W toward the window/liquid interface. If the indices of refraction of the window and the solvent are substantially equal (i.e. within about 0.2 refractive index units of each other) no optical interface exists between the liquid and the window and the ray continues along substantially the same path.

The light ray R' that enters the liquid and strikes a suspended pigment particle is both specularly reflected and diffusely scattered into a solid hemisphere of $2\pi$ radians emanating from a scatter site X. (It is noted that although the scattering occurs within the liquid the scatter site X is illustrated in FIG. 1 at the window/liquid interface). The scattered specular rays, e.g., the ray S, impinges against the window surface E at an angle $\theta_s$ (measured with respect to a normal to that surface) that is less than the critical angle $\theta_c$ of the window/medium interface. Such a scattered specular ray S exits the window (at point Q) into the field of view F presented to a detector.

However, some diffusely scattered rays, e.g. the ray U, which emanate from the scatter site X, impinge against the window surface E at an angle $\theta_U$ that is greater than the critical angle $\theta_c$. Such a diffusely scattered ray U is totally internally reflected within the window (at point V). The diffusely scattered ray U propagates back toward the window/liquid interface where it may undergo a secondary scattering impact at site X', at which point its scattering angle may change direction.

The secondary scattering impact at site X' itself produces specular and diffuse scatterings. Such a scenario is repeated several times within the window material. At each scattering impact some of the light is reflected at angles which would render its direction at the window surface E greater than the critical angle for the window/air interface while some of the light is reflected at angles which would render its direction at the window surface E less than the critical angle for the window/air interface.

The distance d between the initial impact site X and a secondary impact site X' depends on the thickness T of the window W according to the relationship:

$$d = 2 \cdot T \tan \theta_u,$$

where $\theta_u$ is the angle that the diffusely scattered ray U makes with the normal to the surface E.

Owing to the fact that, as discussed earlier, the window must be thick enough to withstand the pressure of the sample stream it may be the case that there is insufficient lateral distance available for a diffusely scattered ray U to undergo a statistically significant number of secondary impacts before being scattered at an angle with respect to the normal to the surface E that is less than the critical angle for the window/air interface. In that case the ray U is more likely to exit through the peripheral surface P of the window W, as indicated at point Z. This energy is outside of the field of view F and is lost to the detector.

The effect caused by total internal reflection of diffusely scattered rays is twofold. Firstly, the intensity of the scattered light ultimately reaching the detector is diminished. This makes the liquid appear darker in color. Secondly, total internal reflection causes the body of the window to exhibit a "glow" effect. This increases the background against which detected radiation is measured.

The diminution in received intensity coupled with an increase in background intensity produces a flattening of the waveform of the intensity/wavelength curve or detected reflectance spectrum. When standard colorimetric calculations are carried out to calculate L*, a* and b* according to the CIELab76 formalism, the net effect of this is to produce a loss of chroma ($C^*_{ab} = [a^{*2} + b^{*2}]^{1/2}$), and to skew the determination of perceived color properties. Moreover, since the intensity undergoes different range distortions in different localized wavelength domains, the problem cannot be expeditiously cured by merely scaling the resulting intensity waveform. Furthermore, if the light is disrupted on its way back to the detector in a way that misrepresents measurement of the true color of the sample, it follows that making adjustments to that color, such as may be required in a manufacturing process, may also be in error.

Accordingly, in view of the foregoing it is believed advantageous to provide an apparatus and a method which mitigates the disruption of light, and hence the loss of chroma, during color measurement of a liquid material using reflectance spectroscopy. It is also believed advantageous that such liquid measurements correlate well to measurements made on the material in its dry state.

It is believed to be of further advantage that the apparatus and method be able to operate in the environment of a pressurized liquid without alteration of the color measurement.

It is believed to be of still further advantage to provide an apparatus where pressurized liquid is introduced into a measurement region without undergoing any flow discontinuity so that a laminar flow of pressurized liquid flow is maintained past the window.

It is believed to be of yet further advantage to provide an apparatus that is able to be cleaned rapidly (e.g., within one or two minutes) so that the cycle time of the measurement is extremely small compared to process changes; that affords easy (including automatic) delivery of a sample to the analysis cell so that measurements of color can be made rapidly; and which can be placed in a potentially hazardous environment, such as a plant floor.

SUMMARY OF THE INVENTION

In a first aspect the present invention is directed toward a method for measuring a color property of a pressurized flowing liquid under test in a way that mitigates the disruption of light. A liquid under test is contacted against a transparent partition that is spaced a predetermined distance from a transparent window. The partition has a predetermined index of refraction and has a thickness dimension that is less than that of the window.

A ray of interrogating radiation having a wavelength within a predetermined range of wavelengths is directed through both the transparent window and the partition into the liquid. At least some of the radiation reflected from the liquid undergoes total internal reflection within the partition while, simultaneously, evanescent coupling of that reflected radiation into the material of the window is prevented.

The prevention of evanescent coupling into the material of the window is accomplished by:
  i) disposing a medium having an index of refraction less than that of the partition between the window and the partition, and
  ii) maintaining the spacing between the window and the partition to a distance not less than three (3) times the wavelength of the interrogating radiation.

Owing to the thickness dimension of the partition, radiation within the partition is afforded the necessary lateral distance to undergo a statistically significant number of internal reflections sufficient to allow that radiation to exit the partition. As a result, more reflected radiation is able to enter the field of view of a detector and be collected thereby than would be the case were the reflected radiation permitted to enter directly into the relatively thicker window. Thus, light disruption and concomitant loss of chroma can be mitigated.

In other aspects the present invention is directed to color measurement apparatus in the form of a flow cell and to a system incorporating the same for measuring the color properties of a liquid flowing through the flow cell using interrogating radiation at a wavelength within a predetermined range of wavelengths.

The flow cell comprises a base and a cover. The cover has a window transparent to interrogating radiation. A thin partition that is also transparent to the interrogating radiation is mounted within the flow cell in spaced relationship between both the window and the base. The partition is preferably formed from a flexible polymer membrane having a first surface and a second surface thereon. The partition has a predetermined index of refraction and has a thickness dimension that is less than that of the window.

The first surface of the partition and the window cooperate to define an air cavity therebetween. reflected from a liquid in a liquid sample chamber. A liquid sample chamber is defined between the second surface of the partition and the base.

The spacing between the partition and the window is such that evanescent coupling of radiation reflected from the liquid into the material of the window is prevented. Thus, at least some of the radiation reflected from the liquid undergoes total internal reflection within the partition. Typically, this spacing is a distance not less than three (3) times the predetermined maximum wavelength in the wavelength range of interrogating radiation.

The partition affords sufficient lateral distance for the reflected radiation to undergo a statistically significant number of reflections before being scattered into an angle less than the critical angle for the partition/air cavity interface. In this way, substantially all of the radiation reflected from the liquid would then traverse the air cavity, enter the window, traverse the window and then exit the window on the side toward the detector, with little disruption to the light and loss of chroma.

A plurality of spacer elements may be disposed in the air cavity to maintain the spaced relationship between the partition and the window.

In accordance with one embodiment of the flow cell of the present invention the spacers take the form of either cylindrical pole-like features or irregular-shaped nodular features formed on the surface of the window. Each such feature thereby defining a spacer element extends from the window toward the partition. The average dimension of each feature measured is approximately one (1) mil (0.001 inch) or twenty-five (25) microns. Each feature is separated from an adjacent feature by an average distance of not less than ten (10) times the average feature dimension.

Alternatively, the spacers may be formed on the first surface of the partition (the surface confronting the window). If the first surface of the partition is a roughened surface, then the irregular roughened features on the partition may serve as the spacer elements.

As yet another alternative, the spacers may take the form of members confined within air cavity that are unattached either to the window or to the partition.

In accordance with still another aspect of the present invention the flow cell has a liquid supply passage and a liquid removal passage formed therein. The liquid supply passage, the sample chamber and the liquid removal passage cooperate to define a liquid flow path through the flow cell. The liquid supply passage, the sample chamber and the liquid removal passage are configured such that any cross section taken in a plane substantially perpendicular to the liquid flow path at any location therealong exhibits substantially the same cross-sectional area.

A system utilizing the flow cell of the present invention includes a reflectance mode spectrophotometer positioned with respect to the flow cell and a pump for pumping a liquid sample therethrough. The spectrophotometer is directs interrogating radiation toward a liquid flowing through the sample chamber and responds to interrogating radiation reflected from the liquid to produce an electrical signal representative of a color property thereof.

In accordance with yet another alternate embodiment of the invention the cover of the flow cell has a pressurized fluid inflow channel and a pressurized fluid outflow channel formed therein. Each of the inflow and outflow channels communicates with the air cavity. The inflow and outflow channels are sized to pass a pressurized fluid, such as pressurized air, through the air cavity such that, in use, the spaced relationship between the partition and the window is maintained by pressurized fluid in the air cavity. The pressure of the pressurized fluid in the air cavity is determined in accordance with the pressure of the liquid flowing through the cell.

In accordance with still another aspect the present invention may be implemented in the form of a probe for measuring a property of a liquid under test using interrogating radiation at a predetermined wavelength. The probe comprises a housing member having a window transparent to interrogating radiation mounted at a first end thereof. A partition transparent to interrogating radiation is mounted in spaced relationship to the window. The partition has a first surface and a second surface thereon, with the first surface of the partition confronting the window. The partition being disposed such that the first surface of the partition and the window cooperate to define an air cavity therebetween. The spacing between the partition and the window is such that radiation reflected from a liquid disposed in contact with the second surface of the partition is prevented from evanescently coupling into the window such that the reflected radiation undergoes total internal reflection in the partition rather than in the window.

BRIEF DESCRIPTION OF THE DRAWINGS

The invention will be more fully understood from the following detailed description taken in connection with the accompanying Figures, which form a part of this application and in which:

FIG. 12 is a schematic representation of a measurement system incorporating a flow cell in accordance with the present invention;

FIG. 15A is a side elevational of a probe implementation of the present invention, while FIG. 15B is an enlarged view of the end of the probe of FIG. 15A.

DETAILED DESCRIPTION OF THE INVENTION

Figure 1:
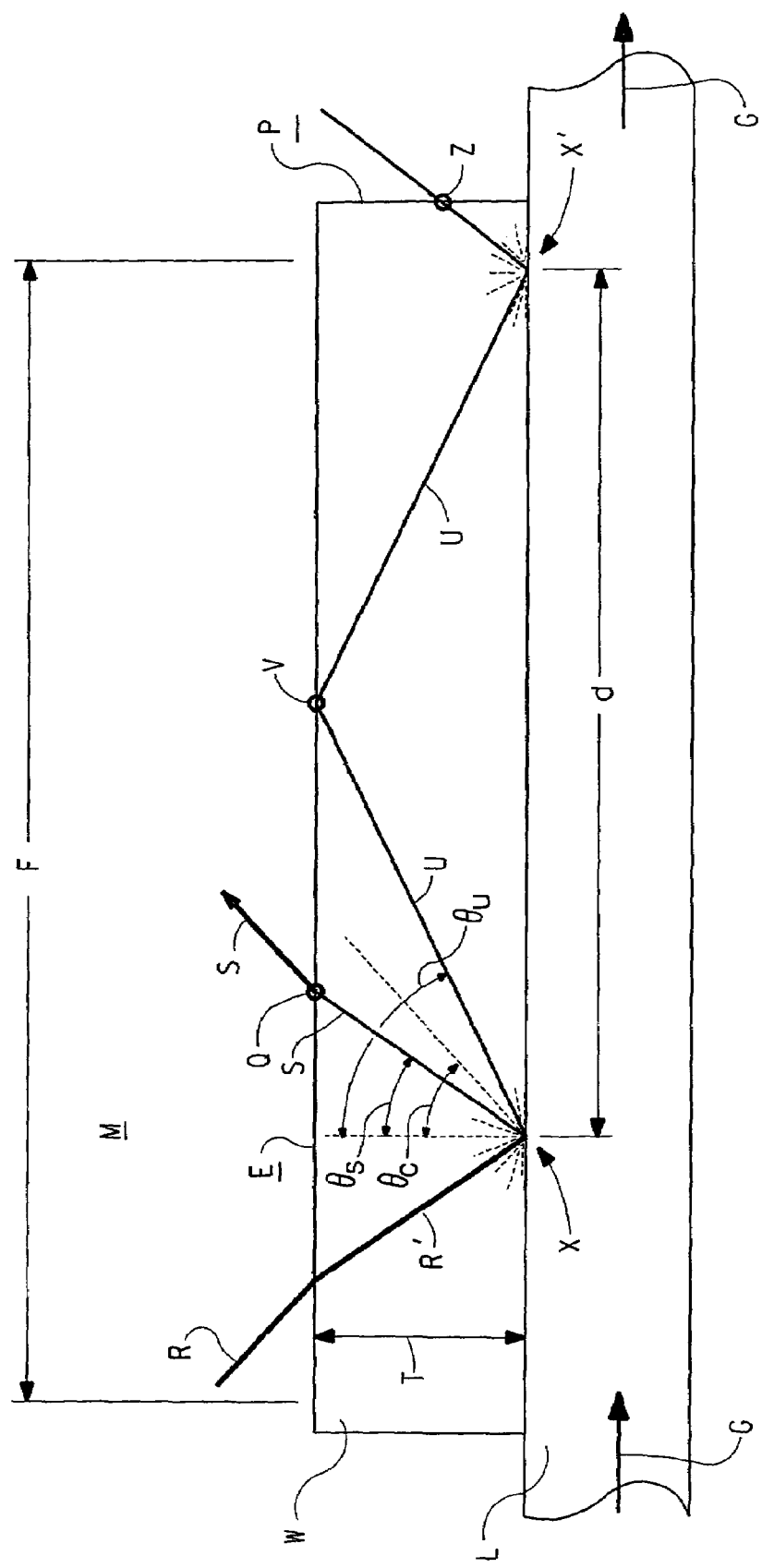
FIG. 1 is a stylized representation of the optical effects at the interface between a window of the flow cell and a liquid in contact with the window of a flow cell of the Prior Art.

Throughout the following detailed description similar reference numerals refer to similar elements in all figures of the drawings. It should be understood that various details of the structure and operation of the present invention shown in various Figures have been stylized in form, with some portions enlarged or exaggerated, all for convenience of illustration and ease of understanding.

Figure 2:
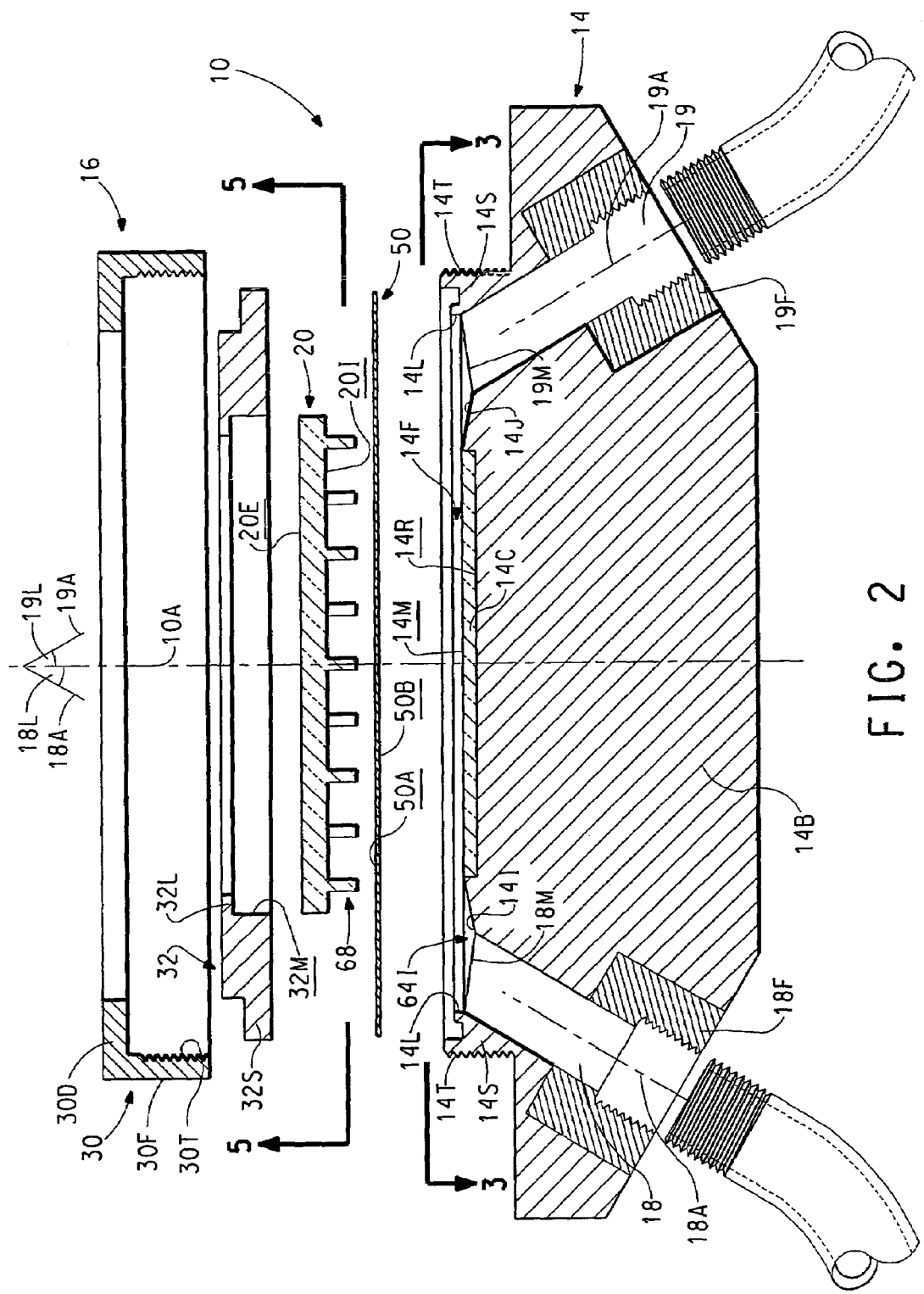
FIG. 2 is an exploded, side elevational view, entirely in section, of a preferred embodiment of a flow cell for measuring a color property of a liquid.

FIG. 2 is an exploded side elevational view, entirely in section, of a preferred embodiment of a flow cell generally indicated by the reference character 10 for measuring a color property of a wet liquid, such as paint, as it flows under pressure through the cell. The measurement is effected by a spectrophotometer 118 (FIG. 12; operating, e.g., in the reflectance mode) using interrogating radiation in a predetermined wavelength range. A suitable interrogating wavelength range is four hundred to seven hundred (700) nanometers. A reference axis 10A extends through the cell 10. It should be understood that although the description herein is cast in terms of the measurement of one or more color properties of liquid paint, the flow cell 10 may be advantageously used to measure other properties of any liquid or gaseous fluid material flowing through the cell.

The flow cell 10 includes an enclosed housing formed from conjoinable first and second housing members 14, 16. In the arrangement illustrated the first housing member 14 defines the base of the flow cell 10 while the second housing member 16 defines a removable cover. One of the housing members, typically the cover 16 in the preferred instance, has a window 20 mounted therein. The window 20 is optically transparent to the interrogating radiation. Liquid under analysis is introduced into the cell 10 through the base 14. However, it should be understood that, if desired, the described arrangement of the parts may be reversed, in which case the window would be disposed in the base and the liquid would be introduced through the cover.

The base 14 includes a body portion 14B machined from stainless steel or any suitable alternative stable material compatible with the liquid whose color properties are being measured. A liquid supply passage 18 and a liquid removal passage 19 extend through the body portion 14B of the base 14. Each passage 18, 19 has a respective axis 18A, 19A extending therethrough. The respective axes 18A, 19A of the respective liquid supply passage 18 and the liquid removal passage 19 define respective angles 18L, 19L (FIG. 1) with respect to the reference axis 10A. The angles 18L, 19L lie within a range from thirty to forty-five degrees (30° to 45°).

Figure 3:
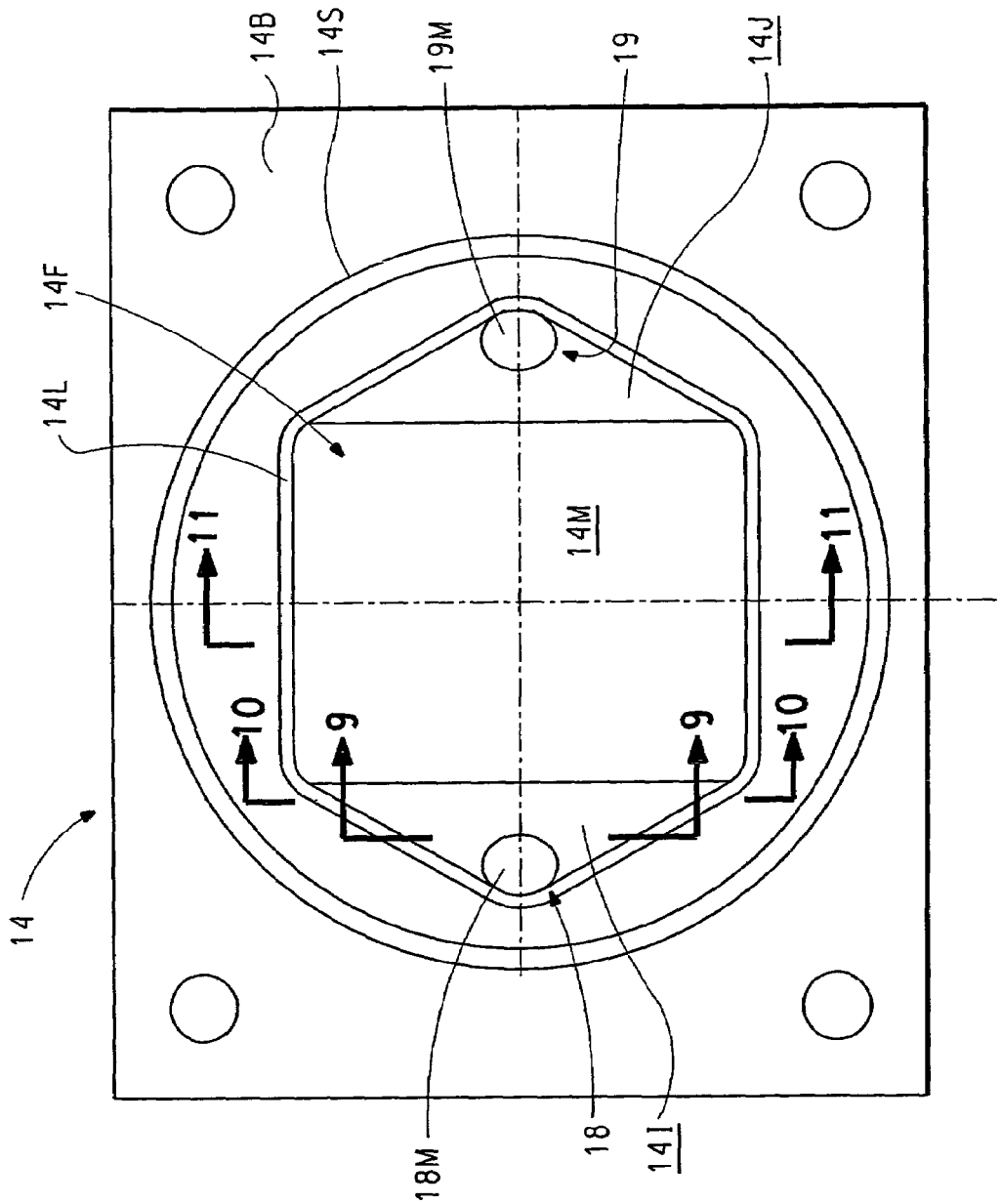
FIG. 3 is a plan view of the base of the flow cell of FIG. 2 taken along view lines 3-3 therein.

As seen from FIGS. 2 and 3 the body 14B is relieved around its periphery to define a mounting boss 14S having external threads 14T (FIG. 2). An upstanding sealing lip 14L is formed on the top surface of the base 14 and encloses a liquid flow area generally indicated by the reference character 14F (FIG. 3). The liquid flow area 14F includes a liquid measurement surface 14M and associated transition surfaces 14I, 14J.

The measurement surface 14M is a generally planar surface that is oriented perpendicular to the axis 10A. The measurement surface 14M occupies the major portion of the liquid flow area 14F. In the preferred instance the measurement surface 14M may be defined by the exposed upper surface of a ceramic insert 14C (FIG. 2) that is cemented into a recess 14R formed in the surface of the body 14B. The ceramic has a glassy surface (preferably white in color) having a reflectivity greater than eighty-five percent (85%).

The transition surfaces 14I, 14J incline from opposed edges of the measurement surface 14M toward the mouths 18M, 19M of the liquid supply passage 18 and the liquid removal passage 19, respectively.

The base 14 is counterbored to accept respective liquid supply and liquid removal fittings 18F, 19F. The fittings 18F, 19F receive respective supply and removal lines 110, 112 (FIG. 12) whereby the flow cell 10 may be connected into a liquid flow circuit.

In the preferred implementation the transition surfaces 14I, 14J, the measurement surface 14M, the interior surface of both the liquid supply passage 18 and the liquid removal passage 19, and the lip 14L are all coated with a thin layer 26 (FIG. 4) of a fluoropolymer material. The layer 26 preferably has a uniform thickness on the order of 0.002 to 0.005 inches (0.0051 to 0.0127 cm). Any suitable fluoropolymer material may be used, provided only that at least the portion 26' of the layer 26 overlying a significant portion of the surface of ceramic insert 14C (if one is provided) is optically clear. A suitable fluoropolymer material for the layer 26 is that fluoropolymer material manufactured by E.I. du Pont de Nemours and Company, Inc., and sold as Teflon® Silverstone. The optically clear layer 26' (if used) may be implemented using that fluoropolymer material manufactured by E.I. du Pont de Nemours and Company, Inc., and sold as Teflon® AF.

Figure 4:
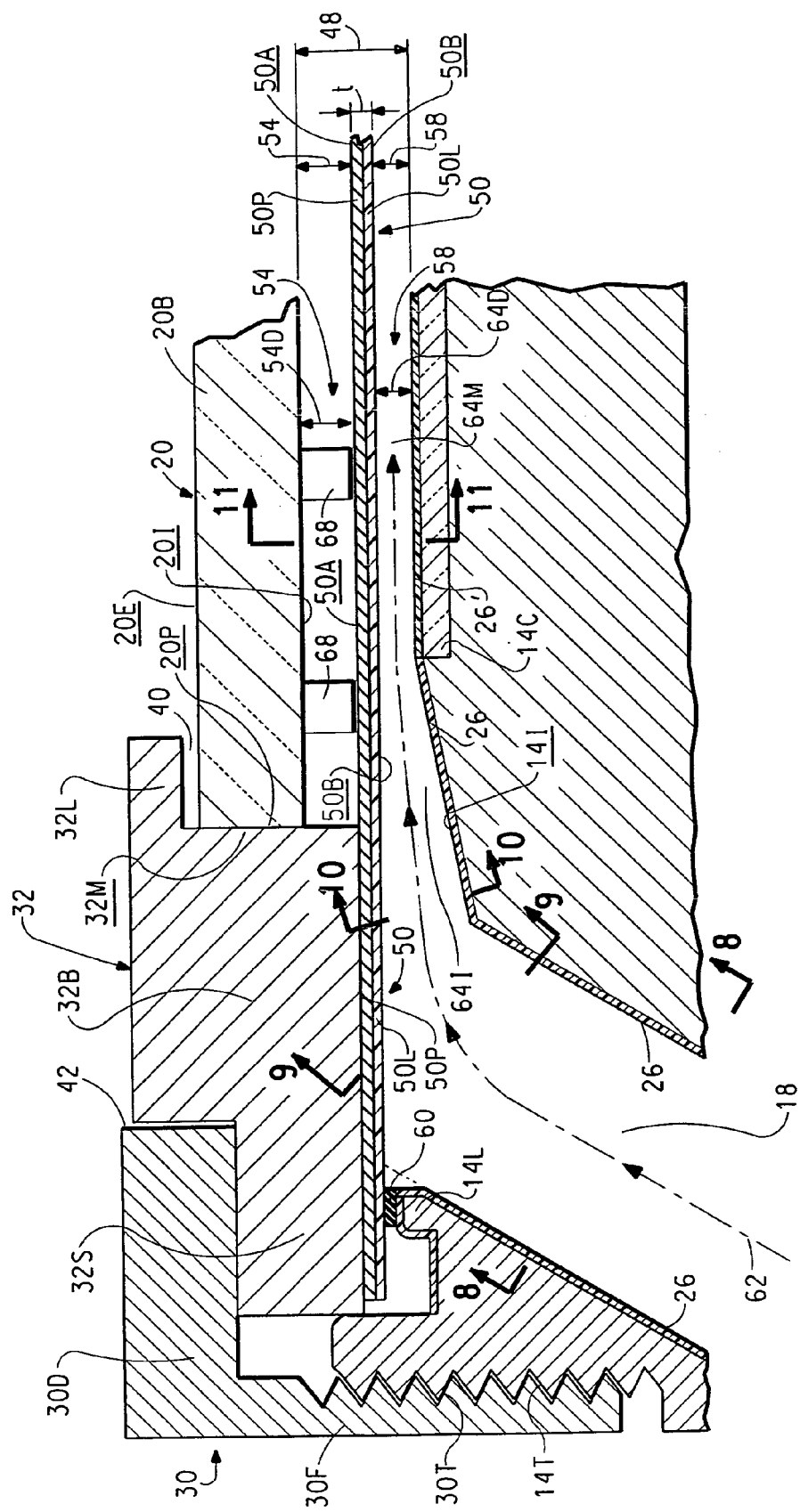
FIG. 4 is an enlarged side elevational view, entirely in section, showing details of the flow cell of the present invention, and in particular, the mounting of partition in spaced relationship between the base and the cover of the cell.

Structurally, as illustrated in FIGS. 2 and 4, the cover 16 includes an outer rim 30 and an annular support ring 32. The support ring 32 receives the generally disc-shaped transparent window 20.

The rim 30 includes an annular disc portion 30D from which a flange 30F depends. Threads 30T are disposed on the interior peripheral surface of the flange 30F.

The main body portion 32B of the support ring 32 has an inwardly extending lip 32L (i.e., extending toward the axis 10A) and an outwardly extending sealing shoulder 32S. The surface of the main body portion 32B beneath the lip 32L defines an annular support surface 32M.

The window 20 includes a main body portion 20B having generally parallel exterior and interior surfaces 20E, 20I, respectively. The window 20 may be formed of quartz, sapphire, or synthetic material such as fused quartz, fused silica or borosilicate. Such materials have an index of refraction on the order of approximately 1.50. This index of refraction is close to the index of refraction of solvents used in the manufacture of liquid paint whose color properties may be measured using the flow cell 10. The peripheral bounding surface 20P of the window 20 is configured to match the support surface 32M on the ring 32.

The threads 30T on the rim 30 are sized to engage the exterior peripheral threads 14T on the mounting boss 14M so that the cover 16 may be removably connected to the base 14. When the cover 16 is threaded onto the base 14 the window 20 is supported in a position overlying the liquid measurement surface 14M.

As best shown in FIG. 4, when the cover 16 is assembled and connected to the base 14, the window 20 is telescopically received by the support ring 32 such that peripheral bounding surface 20P of the window 20 mates against the support surface 32M on the ring 32. The exterior surface 20E of the window 20 confronts the undersurface of the lip 32L of the ring 32. The thickness of the window 20 and the height of the support surface 32M are selected such that a clearance space 40 is defined between the exterior surface 20E of the window 20 and the undersurface of the lip 32L. The space 40 minimizes the possibility of fracture of the window 20 when the cover 16 is treaded onto the base 14. The disc portion 30D of the rim 30 is sized to overlap and act against the sealing shoulder 32S on the support ring 32 as the cover 16 is threaded onto the base 14. The annular gap 42 between the body 32 and the disc portion 30D facilitates threading of the rim 30 to the boss 14S without the occurrence of binding between the rim 30 and the support ring 32.

When the base 14 and cover 16 are fully conjoined the interior surface 20I of the window 20 and the top surface of the base 14 cooperate to define an enclosed interior volume 48.

In accordance with the present invention a transparent partition generally indicated by reference character 50 is mounted within the flow cell 12 in spaced relationship between the window 20 and the base 14. The partition 50 serves to subdivide the enclosed interior volume 48 into a cavity 54 (FIG. 4) and a liquid sample chamber 58.

Perhaps as best seen in FIG. 4 the partition 50 is held in place within the flow cell 10 by the clamping action of the mounting shoulder 32S acting against the mounting lip 14L. If desired, to further insure the sealed integrity of this annular interface a gasket 60 may be provided between the partition 50 and the lip 14L.

The body portion 50P of the partition 50 may be formed from any material that is optically transparent to interrogating radiation at the predetermined wavelength and physically able to confine a pressurized flowing liquid within the liquid sample chamber 58. The partition has an index of refraction on the order of (1.3) to (1.7). In practice the partition is formed from a flexible polymer material, such as a fluoropolymer or polyester. If the partition is formed from a material other than a fluoropolymer, it may, if desired, be coated with a thin layer 50L of an optically clear fluoropolymer material, such as the fluoropolymer material used for the portion 26' of the coating 26. The index of refraction of the layer 50L is close to that of the body portion 50P of the partition 50.

The partition 50 has a first surface 50A and an opposed second surface 50B thereon. The interior surface 20I of the window 20 together with a portion of the mating surface 32M on the support ring 32 cooperate with the first surface 50A of the partition 50 to define the cavity 54. The cavity 54 defines a region adjacent to the interior surface 20I of the window 20 able to receive a material that has an index of refraction that is different (on the order of about 0.2) from that of the partition and the window.

As will be discussed more fully herein the partition is a relatively thin member as compared to the thickness dimension of the window 20. In practice, the partition has a thickness "t" (see also, FIGS. 13A, 13B) in the range from 0.005 to 0.010 inches. (0.0127 to 0.0254 cm).

In the simplest implementation the cavity 54 communicates with the atmosphere so that, in use, the material within the cavity is air. Thus, if the flow cell 10 were operated in the open atmosphere, air would be the material disposed on both sides of the window 20 and refractive effects with reference to the incident radiation would be minimized. However, assuming that any refractive effects are accommodated, it lies within the contemplation of the present invention to dispose within the cavity 54 a material that is different from the atmosphere in which the cell is used. It should be appreciated that the cell may be operated in an atmosphere other than ambient air.

With the partition 50 secured in position a spacing, or gap, is defined between the second surface 50B of the partition 50 and the interior surface 20I. The dimension of gap between the second surface 50B of the partition 50 and the window 20 (measured in a direction parallel to the axis 10A) is indicated by the reference character 54D. The magnitude of the dimension 54D is important. For reasons that are more fully explained herein in connection with FIGS. 13A and 13B the dimension 54D of the gap (measured in a direction parallel to the reference axis 10A) should be, at a minimum, not less than three (3) times the maximum wavelength of the radiation used to interrogate a liquid sample under test. By way of example, if the maximum wavelength of the interrogating radiation is seven hundred (700) nanometers, the dimension 54D should be in the range 2.1 to 3 microns.

The liquid sample chamber 58 is defined between the second surface 50B of the partition 50 and the confrontationally disposed liquid flow area 14F on the base 14. The inside surface of the lip 14L serves as the peripheral boundary of the sample chamber 58. The liquid sample chamber 58 confines a liquid sample as it is flows, under pressure, along a flow path 62 extending from the liquid supply passage 18, through the sample chamber 58 to the liquid removal passage 19. The liquid sample flows from the mouth 18M of the supply passage 18, through an inlet transition region 64I, through a measurement region 64M, and through an outlet transition region 64J (FIG. 14) to the mouth 19M of the removal passage 20. The inlet transition region 64I is defined between the transition surface 14I and the surface 50B of the partition 50. The measurement surface 14M and the surface 50B of the partition 50 cooperate to define the measurement region 64M. The outlet transition region 64J is defined between the transition surface 14J and the surface 50B of the partition 50.

The dimension 64D of the measurement region 64M (measured in a direction parallel to the reference axis 10A) is sized to maintain laminar flow as liquid passes over the measurement surface 14M. Typically, this dimension 64D is on the order of 0.010 inches (0.0254 cm).

In the preferred implementation the dimension 54D of the gap between the second surface 50B of the partition 50 and the interior surface 20I of the window 20 is maintained and flexure or buckling of the partition 50 is simultaneously prevented by the disposition within the air cavity 54 of one or more spacer elements, generally indicated by the reference character 68. The spacer elements 68 may be preferably integrally formed on the interior surface of the body portion 20B of the window 20. It also lies within the contemplation of the invention that the spacers may be formed on the surface 50B of the partition 50 or otherwise physically confined within the air cavity 54 without attachment to either the window or the partition.

Figure 5:
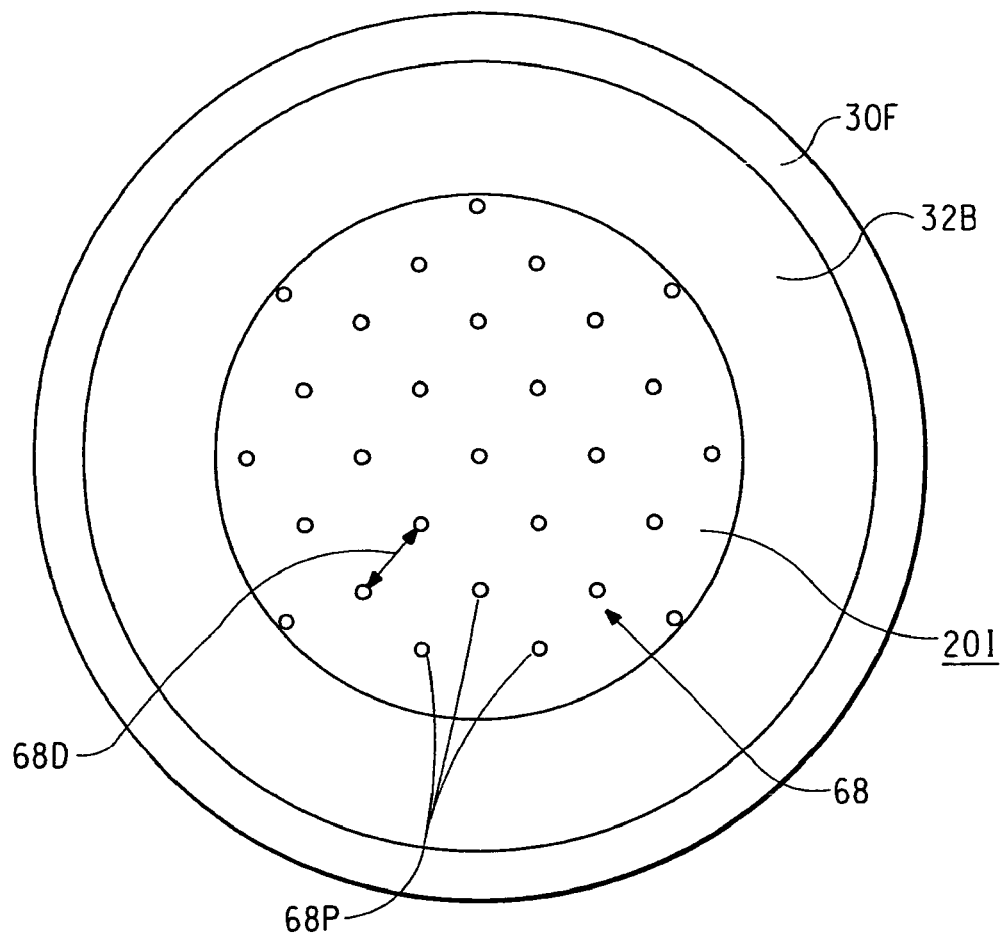
FIG. 5 is a plan view of the interior surface of the window of the assembled cover of the flow cell of FIG. 2, taken along view lines 5-5 in FIG. 2, illustrating the array of pole-like features disposed on the window.

In the embodiment illustrated in FIGS. 3, 4 and 5 the spacers 68 take the form of pole-like members 68P that are integrally formed on the interior surface of the body of the window 20. The pole-like members 68P have generally flattened ends. The members 68P project from the interior surface 20I into the air cavity 54 for a distance sufficient to maintain the predetermined gap dimension 54D of the air cavity 54. Accordingly, consistent with the minimum dimension 54D of the gap the axial length dimension of the members 68P is at least 2.1 to three microns.

In addition to maintaining the dimension 54D of the air cavity 54 the array of pole-like members 68P prevent buckling or bulging of partition 50, thus serving to maintain the optical length of the liquid sample chamber 58 constant throughout the measurement region 64M. (It is noted that in FIG. 4 the flattened ends of the members 68P are shown as spaced slightly from the partition 50 only for purposes of clarity of illustration.)

As best illustrated in FIG. 5 the pole-like members 68P are generally circular in their cross section, having an average diameter on the order of approximately one (1) mil (0.001 inch) [twenty-five (25) microns]. Each pole-like member 68P is separated from an adjacent member by an average distance 68D of not less than about ten (10) times the transverse dimension (e.g., diameter) of the member.

Figure 6:
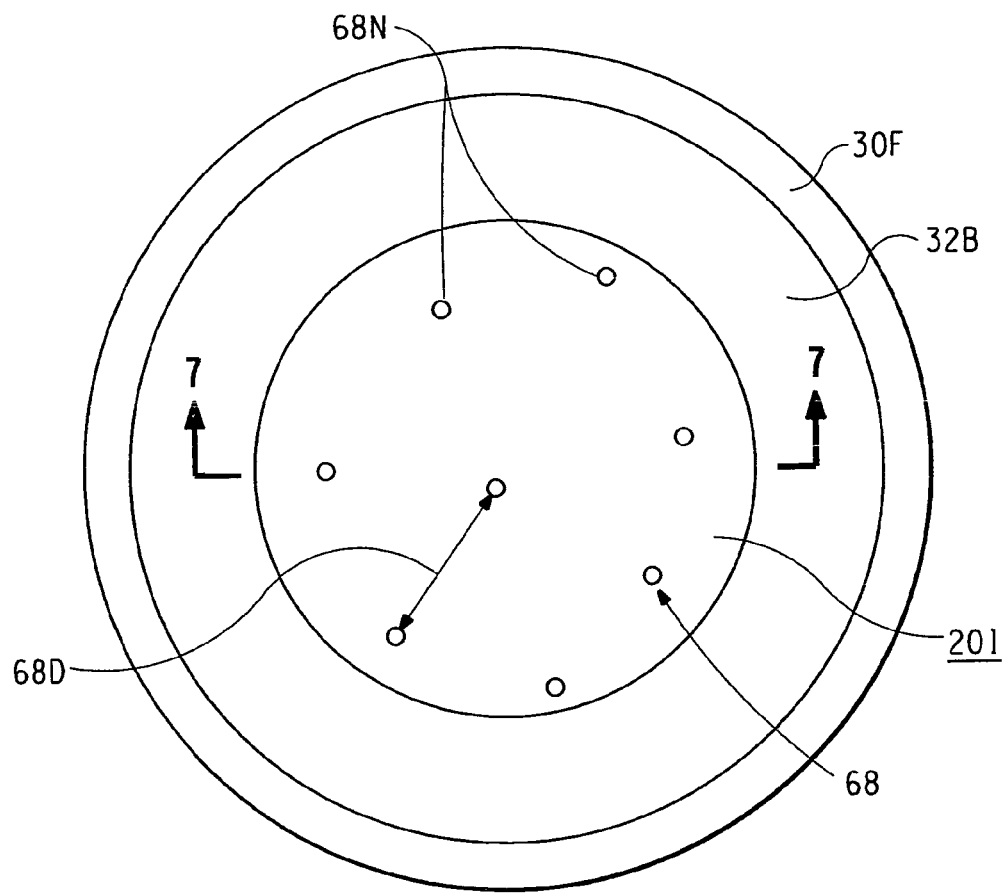
FIG. 6 is a plan view similar to FIG. 5 showing the interior surface of the window of the cover of the flow cell of FIG. 2 and illustrating an array of nodular features disposed on the window.
Figure 7:
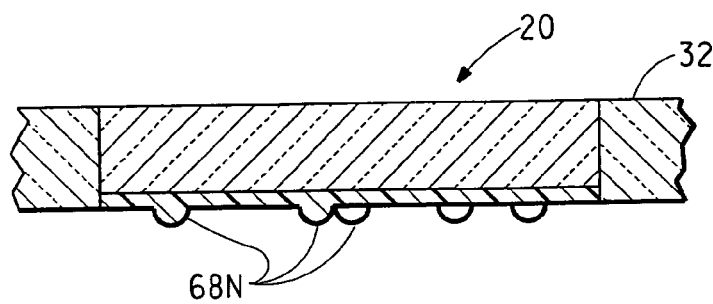
FIG. 7 is a side elevational view, entirely in section, taken along section lines 7-7 in FIG. 6.
Figure 8:
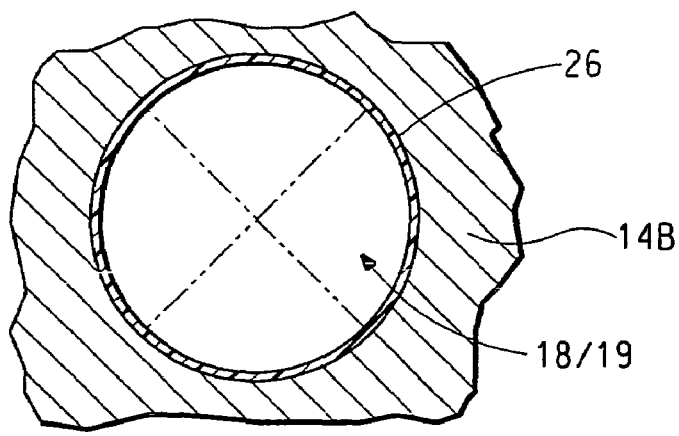
FIGS. 8, 9, 10 and 11 are sectional views, taken along correspondingly numbered section lines in FIGS. 3 and 4, illustrating the configuration of the flow path of a fluid through the flow cell.
Figure 9:
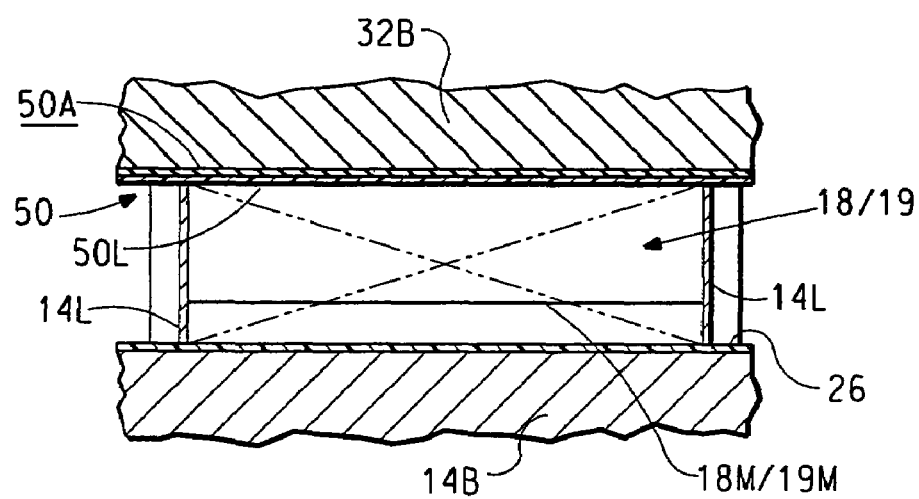
Figure 10:
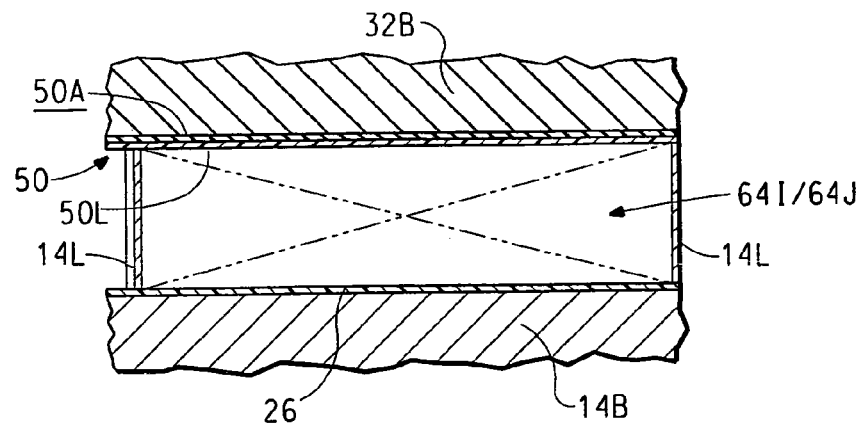

In an alternate embodiment, illustrated in FIGS. 6 and 7, the spacer elements 68 take the form of generally circular, granular nodules 68N. Each nodule 68N is a generally rounded feature that has an average diameter of approximately one (1) mil (0.001 inch) [twenty-five (25) microns] and a height dimension consistent with the minimum dimension 54D of the gap. Each nodule 68N is separated from an adjacent nodule by an average distance of not less than ten (10) times the average transverse dimension (e.g., diameter) of the particle.

Whether implemented in the form of pole-like members 68P or in the form of nodules 68N the spacers 68 should not cover more than three percent to ten percent (3% to 10%) of the area of the interior surface 20I of the window 20. Preferably, the spacers 68 should not cover more than about five percent (5%) of the surface 20I. The spacers 68 may be formed into a regular formation (as illustrated in the case of the pole-like members 68P) or as a randomly disposed array (as illustrated in the case of the nodules 68N).

The pole-like members 68P or the nodules 68N are preferably formed on the body of the window using photolithographic techniques. In general, a photolithographic technique involves deposition of a layer of a polymeric photoresist material the inner surface of the window 20. A photomask having a desired pattern of regular or random features is laid over the photoresist. For example, the photomask may be created by using the nodular surface on one side of the ink jet printer transparency available from Hewlett-Packard Inc. and sold as model HP C3834A Premium Inkjet Transparency Film as the template for the photomask. The photoresist is exposed to actinic radiation with the mask in place, resulting in the production of polymerized and non-polymerized areas in the polymer layer. Unwanted material in the pattern is chemically dissolved from the photopolymer layer, leaving the resulting pattern of spacers.

In one particular fabrication technique a fused silica disk used for the window is subjected to a modified "RCA-type" cleaning in a wet cleaning station to remove organics and metal contamination. "RCA clean" is an industry standard developed by RCA Company for removing contaminants from wafers. The silica disk is dipped for ten (10) minutes into a 65° C. bath containing $NH_4OH:H_2O_2:H_2O$ in a 1:1:6 ratio. After the disk is rinsed for ten (10) minutes with de-ionized water it is dipped for ten (10) minutes into an 85° C. bath containing ninety-five percent (95%) $H_2SO_4$. It is rinsed for fifteen (15) minutes with de-ionized water and blown dry with nitrogen. The disk is then dehydrated under vacuum and heat and cooled in a dry nitrogen atmosphere to prepare for film deposition.

Post spacers are formed using a photoresist and a phototool. A suitable photoresist is that available from Microchem Incorporated, Newton, Mass. as NANO™ SU-8 2000 Negative Tone Photoresist. This epoxy-based resist is available in various viscosities for spinning different thickness ranges. Basically, the percentage of solvent (cyclopentanone) is adjusted to achieve the correct viscosity. This photoresist contains a photoinitiator and sensitizer which is "dialed in" to a 365 nm I-line UV.

Using a spinner apparatus such as that available from Headway Research, Inc., Garland, Tex., the photoresist is applied to the surface of the disk. Spin conditions are determined by the desired height of the spacer. The resist is softbaked using a two-step hotplate bake at temperatures of 65° C. and 95° C., respectively. Bake time is dependant on the resist thickness.

The cooled disks are then imaged on a UV exposure unit such as that available from Optical Associates Inc., San Jose, Calif. as the OAI Hybralign™ Series 500 Mask Alignment and Exposure System. The UV is 365 nm I-line UV. Power level for is 5 mW/cm2; exposure time is dependant on resist thickness.

A post-exposure bake follows. This is a two-step hotplate bake, 65° C. and 95° C. respectively. Bake time is dependant on the resist thickness. The disks are allowed to cool slowly and are immersion-developed in an SU8 Developer available from Microchem Incorporated. This developer is a solvent, PGMEA (Propylene Glycol Monomethyl Ether Acetate).

After inspection the patterned disks are hard baked in a laboratory oven. The temperature is ramped up to 175° C., held for two (2) hours and ramped down to ambient.

The spacers may also be formed on the surface of the window using any other suitable microfabrication process.

In an alternate embodiment the spacer elements may be integrally formed on the second surface of the partition. For example, if a polyester base sheet from an ink jet printer transparency (with any adhesive coating stripped from the front surface) is used to implement the partition, the opposite surface of the sheet may exhibit a nodular surface sufficient to maintain the spacing of the partition from the window. The ink jet printer transparency available from Hewlett-Packard Inc. and sold as model HP C3834A Premium Inkjet Transparency Film is useful for this purpose.

In still another alternate embodiment the spacer elements may be disposed within the cavity 54 unattached to either the window or to the partition.

In order to maintain a laminar flow of the liquid through the sample chamber 58 it is important that no flow disruptions be presented to a liquid as it progresses along the flow path 62.

To this end the liquid supply passage 18, the liquid removal passage 19, the inlet transition region 64I, the measurement region 64M, and the outlet transition region 64J are all configured such that any cross section taken in a plane substantially perpendicular to the liquid flow path at any location therealong exhibits substantially the same area.

Figure 11:
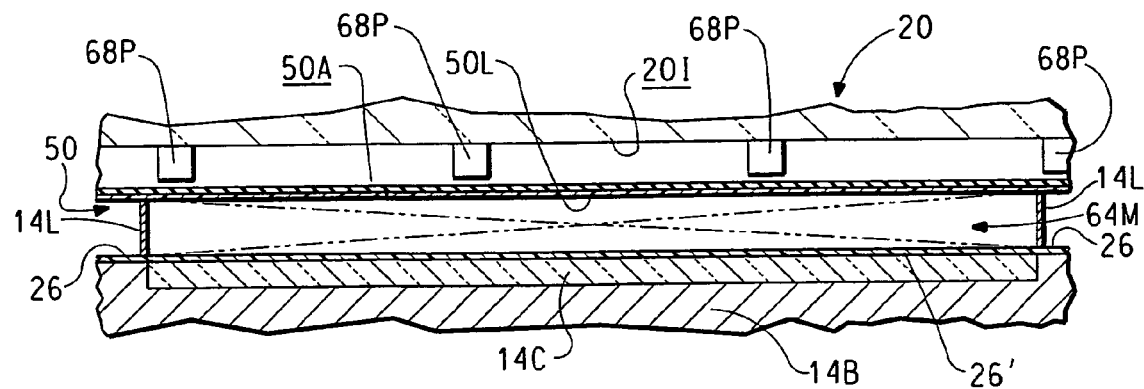

This construction is illustrated in the series of elevational views shown in FIGS. 8 through 11. These various views illustrate the configuration of the liquid supply passage 18 within the body 14B of the flow cell (FIG. 8), at the mouth 18M of the liquid supply passage 18 (FIG. 9), in the inlet transition region 64I (FIG. 10), and in the measurement region 64M (FIG. 11). Since the construction of the cell 10 is symmetrical the configuration of the flow path 62 in the an outlet transition region 64J, at the mouth 19M of the liquid removal passage 19, and in the liquid removal passage 19 are identical to the configurations shown in FIG. 10, FIG. 9 and FIG. 8, respectively.

In the preferred instance the liquid supply passage 18 and the liquid removal passage 19 are each formed as substantially circular bores extending through the body 14B. Thus, the cross sections through the passages (e.g., FIG. 8) are circular in shape. Owing to the geometry of the cell 10 the cross sections at the mouth 18M, 19M of the respective passages 18, 19, in the transition regions 64I, 64J, and in the measurement region 64M, are substantially rectangular in shape (e.g., FIGS. 9 through 11). The geometry of the cell is such that the areas of these cross sectional planes are substantially equal. Thus, a liquid encounters no flow discontinuity as it is pumped along the flow path 62.

It also lies within the contemplation of this invention that the liquid supply passage 18 and the liquid removal passage 19 may each be alternately configured as rectangular in shape. In this arrangement each passage may be formed from confronting pairs of substantially planar walls. The walls in at least one confronting pair of planar walls converge toward the passage axis over the length of the passage such that a uniform cross sectional area in a plane perpendicular to the passage axis is maintained at each point therealong.

FIG. 12 is a schematic representation showing the flow cell 10 in accordance with the present invention as utilized within a spectrophotometric system generally indicated by the reference character 100 for measuring a property of a pressurized flowing fluid. The fluid could be any liquid or gaseous fluid whose properties it is desirable to ascertain and to monitor. In the present discussion it is assumed that the color properties of liquid paint or tint are being ascertained and monitored.

The components of the liquid material are metered into a vessel 102 and combined by the mixing action imparted by a mixing blade 104. The liquid material is circulated by a pump 108 through a recycling flow path defined by a piping loop 106. Instead of a pump, a pressurized fluid (e.g., pressurized air) may be used to move liquid from a closed container along the flow path 106. The flow path 106 may have one or more mounting openings 108A, 108B provided in predetermined locations along the flow path for purposes to be described.

In one arrangement the flow cell 10 is connected into the recycle loop 106 by an inlet connection line 110 and an outlet connection line 112. The connection lines 110, 112 are respectively received by the fittings 18F, 19F provided in the cell 10 (FIG. 1). Respective pressure sensors 114, 116 may be provided to monitor the pressure in the connection lines 110, 112.

As the liquid flows through the liquid sample chamber 64 it is interrogated by a spectrophotometer 118. The spectrophotometer is operative to direct interrogating radiation toward the fluid flowing through the sample chamber of the cell and to respond to interrogating radiation reflected from a fluid to produce an electrical signal representative of a property thereof. If desired, the spectrophotometer may be arranged in a manner that utilized three directions of measurement, as disclosed in U.S. Pat. No. 4,479,718 (Alman), assigned to the assignee of the present invention.

The particular spectrophotometer utilized is dependant upon the nature of the liquid sample being measured. For the color measurement of liquids containing effect pigments, the preferred spectrophotometer may be arranged in a manner such that several (two or more) detectors are positioned at multiple respective angles with respect to the specularly reflected ray. Each detector is positioned either:

1) within the plane defined by the illuminating ray and the specularly reflected ray (hereafter referred to as the plane of illumination); or
2) out of said plane at multiple respective azimuthal directions with respect to said plane, and at multiple respective predetermined angles of declination with respect to the plane of sample flow through the sample flow chamber.

In the latter instance, the spectrophotometer would be a goniospectrophotometer. As an example of the former, in the measurement of liquids containing metallic pigments, a spectrophotometer which has detectors at three directions of measurement as above, as disclosed in U.S. Pat. No. 4,479,718 (Alman), assigned to the assignee of the present invention, may be utilized.

Further color information may be obtained by orienting the flow cell 10, herein described, such that measurements may be made, wherein the flow direction through the cell is inclined at any arbitrary azimuthal angle with respect to the plane of illumination described above.

It is also assumed that the spectrophotometer 118 has been calibrated either by a suitable off-line calibration procedure or by interrogating the surface of the measurement plaque (if one is provided).

Figure 13A:
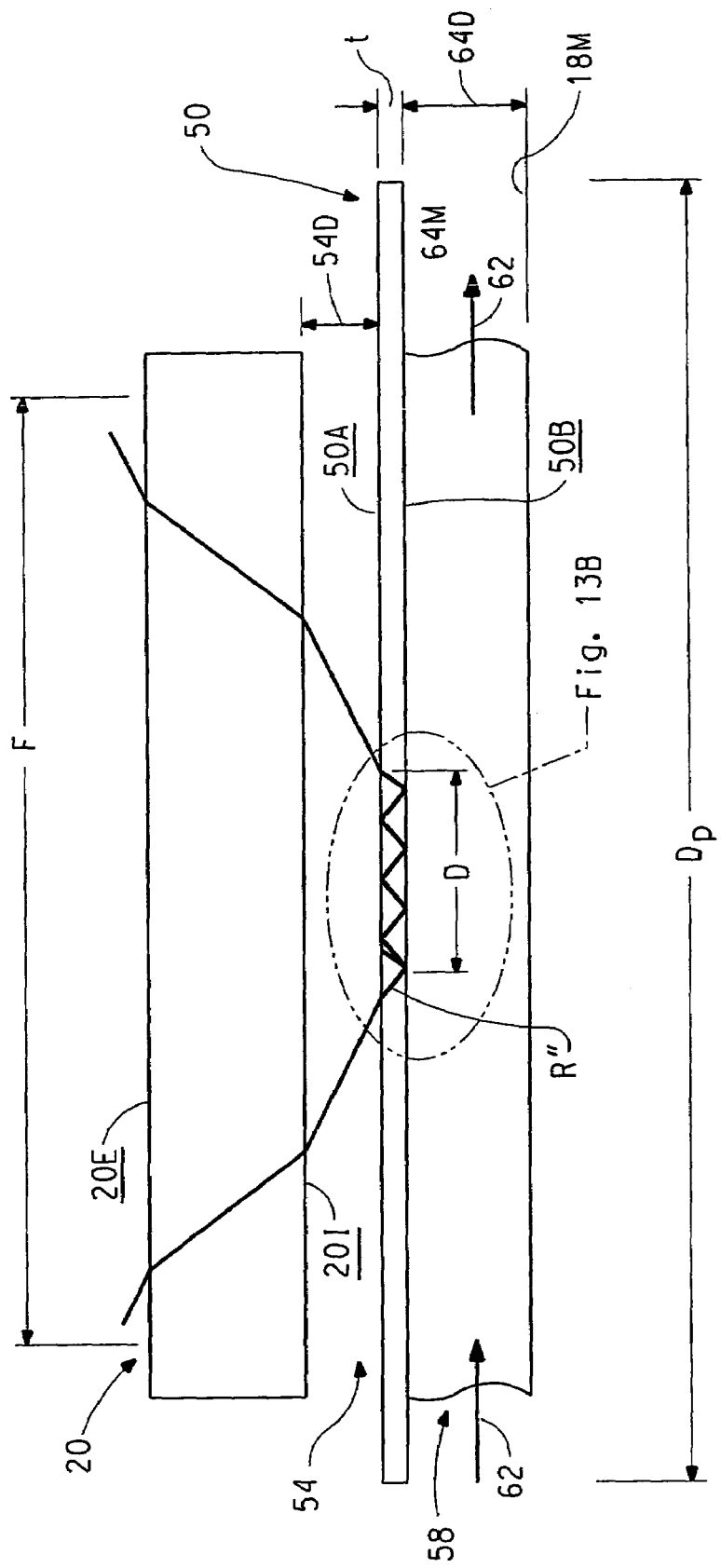
FIGS. 13A and 13B are stylized representations, similar to FIG. 1, showing the optical interactions occurring within a flow cell of the present invention.

FIG. 13A is a ray diagram, similar to FIG. 1, illustrating the optical operation of the flow cell of the present invention. An incident ray R of interrogating radiation at a predetermined wavelength propagates toward the exterior surface 20E of the window 20. The material of the window 20 has an index of refraction that is greater than the index of the medium surrounding the cell. Upon striking the surface 20E the disparity in indices of refraction between the medium above the window and the material of the window produces a refracted ray R'. The refracted ray R' propagates through the window until it encounters the interior surface 20I of the window. As the ray exits the window the disparity in indices of refraction between the material of the window and the material within the cavity 54 again causes the ray to be refracted. To minimize refractive effects it is preferable that the medium M and the material within the cavity 54 are the same (e.g., ambient air). The resulting refracted ray then propagates toward the partition 50 with the same angle of inclination to the axis 10A as the ray R.

The ray R propagates through the cavity 54 toward the surface 50A of the partition 50. The ray R is refracted by the material of the partition 50. The refracted ray R" exits the surface 50B and interacts with the liquid material in the sample chamber 58.

If the ray R" encounters a pigment particle or other scattering entity in the liquid the ray R" will be specularly reflected and diffusely scattered, similar to the interaction occurring at scatter site X in FIG. 1. The specularly reflected radiation will exit the upper surface 50A of the partition and propagate through the cavity 54 toward the window 20.

If the dimension of the cavity 54 is sized so as to prevent diffusely scattered radiation from evanescently coupling into the window 2 the diffusely scattered radiation will undergo total internal reflection in the partition. Owing to the thickness "t" of the partition (relative to the thickness of the window) there is sufficient lateral distance D along the plane of the partition for the internally reflected radiation to undergo a statistically significant number of secondary scatterings. The likelihood that the radiation will be re-scattered at an angle less than the critical angle of the interface between the partition and the cavity material is increased. Thus, the probability that a larger proportion of the totally internally reflected energy will exit the window 20 is enhanced.

Appropriately selecting the dimension 54D of the gap between the window 20 and the partition 50 to prevent light in the partition from evanescently coupling into the window thus increases the amount of diffusely scattered radiation that will be harvested by the detector. The window and partition must be kept separate by a sufficient dimension 54D so as to prevent frustration of the total internal reflection occurring within the partition. This latter effect, called frustrated total internal reflectance, is in reality leakage of the electric field of the radiation being totally internally reflected in the partition into the window material, and occurs when the two materials with similar indices of refraction are in close-to-intimate contact, to the extent that their respective juxtaposed surfaces are separated by a distance less than a small multiple of the penetration depth, /, of the radiation into the rarer medium (in this case the gap between the partition and the window), or the distance required for the evanescent wave amplitude to drop to 1/e of its value in the rarer medium. This penetration depth, "/", is governed by the relation:

$$l = \frac{\lambda \cos\theta_u}{2\pi n_{gap}\sqrt{[(n_{partition}/n_{gap})\sin\theta_u]^2 - 1}}$$

where $\lambda$ is the maximum wavelength of light;

$n_{partition}$ is the index of refraction of the partition $n_{gap}$ is the index of refraction of the gap between the partition and the window, and $\theta_u$ is the angle of incidence of the totally internally reflecting light rays within the partition with respect to the normal to the interface between the partition and the gap.

A general rule of thumb for guaranteeing that a sufficient distance is maintained between two dense media separated by a rarer medium, so as to prevent frustrated total internal reflection, is to separate the two dense media by a dimension 54D not less than three (3) times the maximum interrogating wavelength.

Turning now to the thickness dimension "t" of the partition 50, it is important that this thickness dimension be fairly thin. To answer the question of how thin it should be, it is important to recall the issue of why a relatively thick window with an index of refraction close to the index of the material being measured disrupts the light so that the detector misrepresents the true color of the material, which it would see if no window were present and if it were viewing the free surface of the material. As noted above in connection with the discussion of FIG. 1, the reasons are that:

1) some light escapes through the window edges, thus decreasing the lightness of the object as seen by the detector since some radiation never reaches it, and 2) the window glows due to stray scattering from the window edges, thus raising the background or baseline of the reflectance spectrum detected.

Both of these phenomena are mitigated if a partition is interposed between the window and the material being measured, and if within the partition, the light is somehow prevented from escaping the field of view F of the detector, as shown in FIG. 13A. In the discussion that follows it is assumed that the lateral dimension of the field of view F of the detector is smaller than the lateral dimension of the partition, $D_p$.

In order to accomplish this, it being established that some of the diffusely scattered light from the material being measured suffers total internal reflection within the partition, one must assure that the lateral distance D traversed by any given scattered ray within the partition before re-emergence, defined as in FIG. 13A, is less than F/2.

Figure 13B:
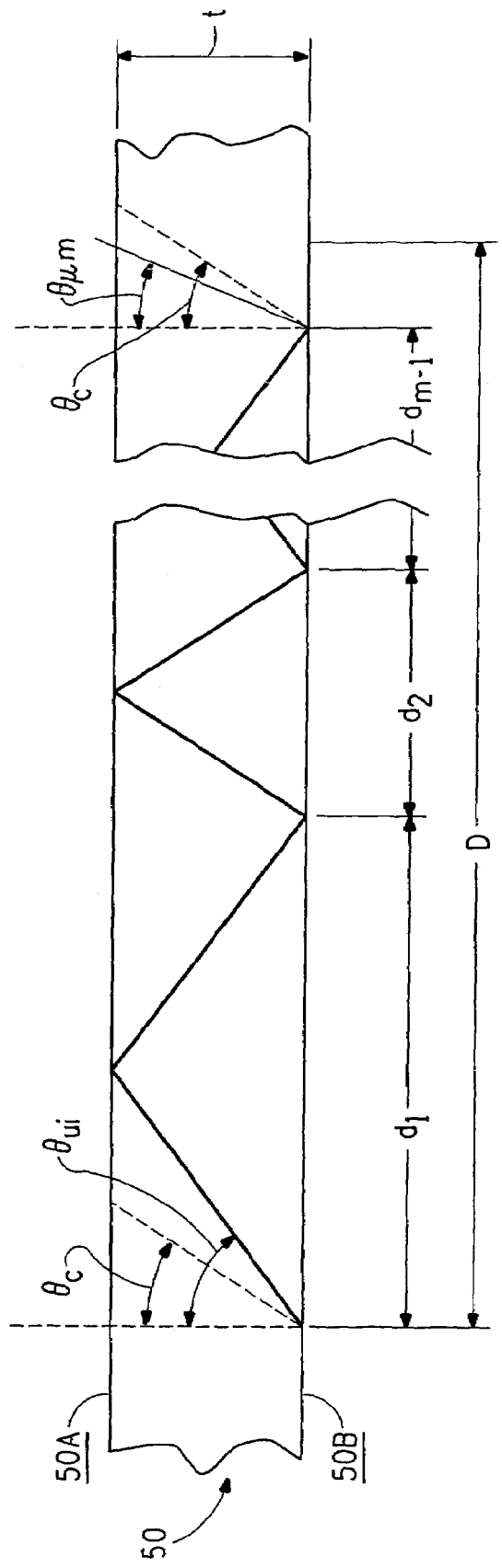

With reference to FIG. 13B, it is noted that the total distance D traversed by a diffusely scattered and totally internally reflected ray is comprised of several segments, $d_1$, $d_2$ and etc., or $d_i$ in general, due to the fact that said ray can scatter at different angles $\theta_{u1}$, $\theta_{u2}$, and etc., or $\theta_{ui}$ in general, at surface 50B at the different points of contact with the material being measured. The angles $\theta_{ui}$, as noted above, are the scattering angles of a ray which scatters in an angular direction greater than the critical angle $\theta_c$ with respect to the system normal for the partition/air cavity interface at the surface 50A, as the ray being considered is assumed to be totally internally reflecting. Now $\theta_c$, the critical angle for the partition/air cavity interface, is defined as follows:

$$\sin\theta_c = \frac{n_{gap}}{n_{partition}}$$

with $$\theta_c \leq \theta_{ui} \leq \pi/2$$

If the ray makes m bounces within the partition, being totally internally reflected on each bounce except for the $m^{th}$, whereupon it re-emerges through the upper surface 50A of the partition 50, the total distance D traveled in the transverse direction along the lateral dimension of the partition is given by:

$$D = d_1 + d_2 + \ldots + d_m = \sum_{1}^{m} d_i$$

From geometrical considerations, the $d_i$ up to but not including $d_m$, can be calculated from the partition thickness dimension t and the scattering angle $\theta_{ui}$ as:

$$d_i = 2t \tan \theta_{ui}$$

Assuming that, after the $m^{th}$ bounce, the ray re-emerges through surface 50A, $d_m$ therefore has a minimum value of 0, and a maximum value given by:

$$d_{m\ max} = t \tan \theta_c$$

Thus, the criterion for the thickness of the partition can now be set as:

$$D = \left(2t \sum_{1}^{m-1} \tan\theta_{ui}\right) + t\tan\theta_m \leq F/2$$

or $$t \leq \frac{F/2}{\left(2\sum_{1}^{m-1} \tan\theta_{ui}\right) + \tan\theta_m}$$

Assuming that the field of view F is set by the spectrophotometer manufacturer, the maximum thickness t of the partition may be found by minimizing the right hand side of the inequality and, therefore, maximizing the denominator of the above expression. Obviously, if all of the $\theta_{ui}$ to $\Pi/2$, and $\theta_{m=\theta_c}$, the denominator tends to infinity, and t goes to 0, which just says that a free surface measurement would capture all of the light possible.

However, in practical terms, if it is desired to contain the sample in a closed system, the question may be case in terms of the percentage of the diffusely scattered light desired to be captured. It is presumed that specularly scattered light will re-emerge from surface 50A after the first scattering encounter, since its angle of scatter is $\theta_r$, the refracted angle in the partition, which is by definition less than $\theta_c$.

For the diffusely scattered light, therefore, if it is assumed that the measured sample is a Lambertian scatterer, and hence, all scattering angles are equally probable, and in a near-worst case scenario in which maximal lateral distance, $d_i$, per scattering encounter with surface 50B is suffered by the internally reflecting/scattering ray, from a practical standpoint therefore, setting $\theta_{ui}$ all equal to a high percentage of their maximum possible value of $\Pi/2$, which herein termed $\theta_{umax}$, and set $\theta_m = \theta_c$, in order to maximize the denominator of the inequality for "t" above, but not have it approach infinity. The expression for "t" then becomes:

$$t \leq \frac{F/2}{\left(2\sum_{1}^{m-1} \tan\theta_{umax}\right) + \tan\theta_c} = \frac{F/2}{(2(m-1)\tan\theta_{umax} + \tan\theta_c)}$$

or, utilizing the definition of the critical angle, $$t \leq \frac{F/2}{\left(2(m-1)\tan\left(p\frac{\pi}{2}\right) + \tan\left(\sin^{-1}\frac{n_{gap}}{n_{partition}}\right)\right)}$$

where p is a percentage close to 90%-100%.

To determine what value of m, the number of scatterings within the partition, should be used in the above expression, one needs to consider the probability of a ray, once making an encounter with a scattering center at the boundary 50B, scattering into an angle greater than the critical angle versus the probability of said ray scattering into an angle less than the critical angle. Again if one assumes the measured material to be Lambertian scatterer, diffuse scattering should be isotropic, and hence all angles equally probable. That being the case therefore, the probability, $P(\theta_{ui} \geq \theta_c)$, of a ray scattering into an angle greater than the critical angle for the partition/air cavity interface at a scattering center i is given by:

$$P(\theta_{ui} \geq \theta_c) = \frac{\int_{\theta_c}^{\frac{\pi}{2}} d\theta}{\int_0^{\frac{\pi}{2}} d\theta} = \frac{(\frac{\pi}{2} - \theta_c)}{\frac{\pi}{2}} = \frac{2}{\pi}\left(\frac{\pi}{2} - \theta_c\right)$$

Similarly, the probability $P(\theta_{ui} \leq \theta_c)$ of a ray scattering into an angle less than the critical angle as above is:

$$P(\theta_{ui} \leq \theta_c) = \frac{\int_0^{\theta_c} d\theta}{\int_0^{\frac{\pi}{2}} d\theta} = \frac{\theta_c}{\frac{\pi}{2}} = \frac{2}{\pi}(\theta_c)$$

Therefore, the probability of a light ray being emergent at surface 50A of the partition after m scattering events is just the cumulative combined probabilities of:

1) the probability of the ray scattering into an angle greater than the critical angle for m−1 scattering events, and
2) the probability of the ray scattering into an angle less than the critical angle on the mth scattering event, or mathematically:

$$P_m(\theta_{um} \leq \theta_c) = \sum_{i=1}^{m} P(\theta_{ui} \leq \theta_c)[P(\theta_{ui} \geq \theta_c)]^{i-1}$$

or $$P_m(\theta_{um} \leq \theta_c) = \frac{2}{\pi}\theta_c \sum_{i=1}^{m}\left[\frac{2}{\pi}\left(\frac{\pi}{2} - \theta_c\right)\right]^{i-1} = \frac{2}{\pi}\theta_c \sum_{i=1}^{m}\left[\frac{2}{\pi}\left(\frac{\pi}{2} - \theta_c\right)\right]^{i-1}$$

Performing the summation, this then reduces to:

$$P_m(\theta_{um} \leq \theta_c) = \frac{2}{\pi}\theta_c \frac{\left[1 - \left[\frac{2}{\pi}\left(\frac{\pi}{2} - \theta_c\right)\right]^m\right]}{\left[1 - \left[\frac{2}{\pi}\left(\frac{\pi}{2} - \theta_c\right)\right]\right]}$$

This expression can then be inverted to solve for m, given a desired percentage of the light, $P_m(\theta_{um} \leq \theta_c)$, that is re-emergent after m scattering events and collected by the detector. We have:

$$m = \frac{\log\left\{1 - \frac{P_m(\theta_{um} \leq \theta_c)\left[1 - \frac{2}{\pi}\left(\frac{\pi}{2} - \theta_c\right)\right]}{\frac{2}{\pi}\theta_c}\right\}}{\log\left\{\frac{2}{\pi}\left(\frac{\pi}{2} - \theta_c\right)\right\}}$$

From these expressions then, the maximum thickness "t" of the partition may be estimated by making some assumptions. For example, if it is first assumed that the gap is composed of air, then $n_{gap}=1$. Furthermore, if it is assumed a polyester material for the partition, $n_{partition}=1.65$, and $\theta_c$ then becomes 37.3°. Finally, if it is desired to collect 90% of the light, $P_m=0.9$, and m, the number of bounces necessary to achieve this, becomes:

$$m = \frac{\log\left\{1 - \frac{0.9\left[1 - \frac{52.69}{90}\right]}{\frac{37.31}{90}}\right\}}{\log\left\{\frac{52.69}{90}\right\}} = 4.3$$

where it is recognized that the factors which begin with $2/\Pi$ are actually ratios of angles and where the angles have been converted to units of degrees. A common field of view for reflectance spectrophotometers is $F=0.5"$. Further assuming that at each scattering event the scattering angle is 90% of p/2 for maximal lateral distance traversed per scattering event, one can then substitute this result into the expression above for t, and obtain:

$$t \leq \frac{0.5''/2}{(2(4.3-1)\tan(0.9\times 90°) + \tan(37.31°))} = 0.00589''$$

Figure 14:
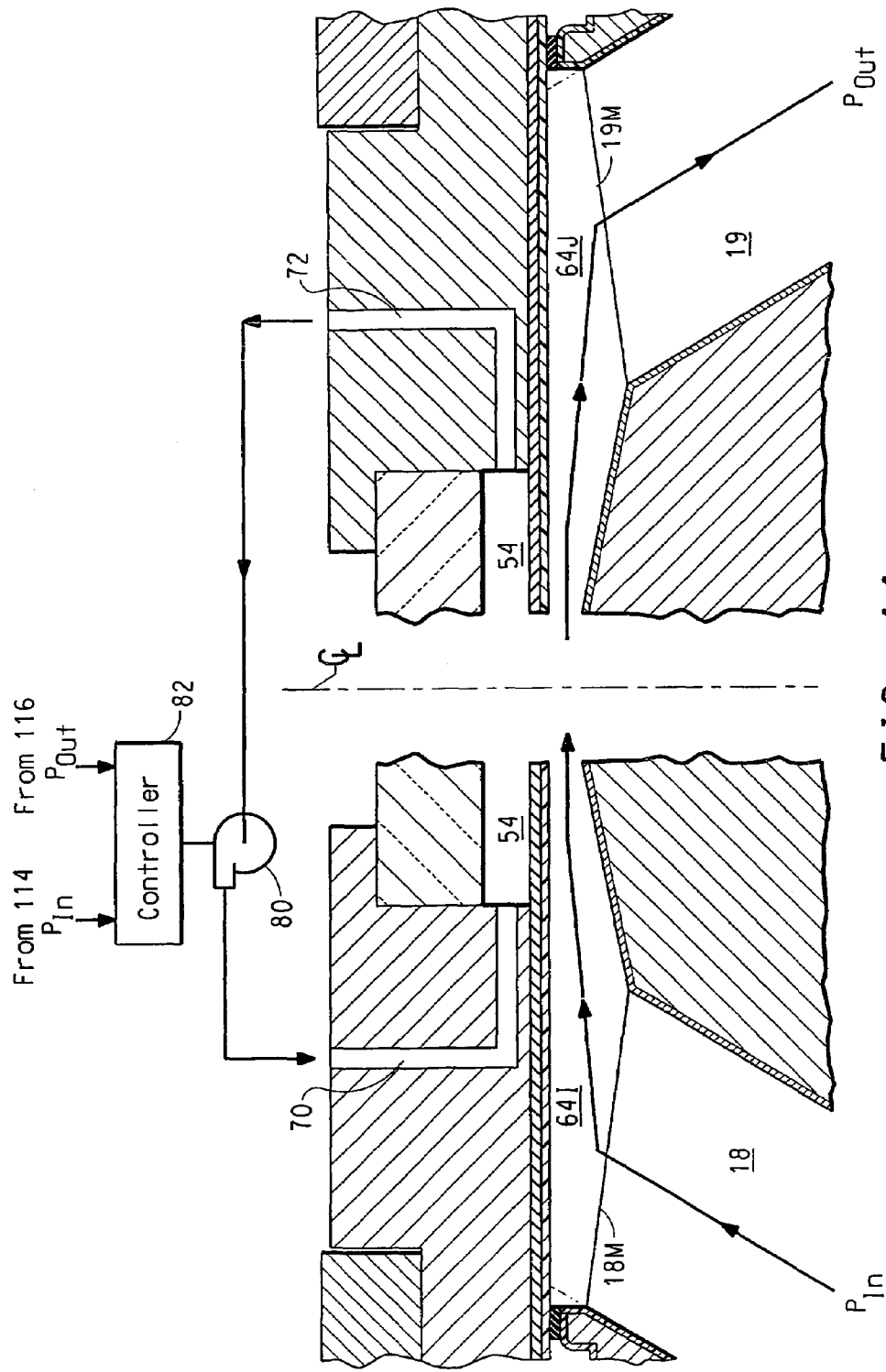
FIG. 14 is an enlarged side elevational illustrating an alternate embodiment of the flow cell of the present invention in which the cover of the flow cell has a pressurized fluid inflow channel and a pressurized fluid outflow channel formed therein.

FIG. 14 illustrates still another alternative embodiment of a flow cell in accordance with the invention. In this embodiment the cover 16 is provided with at least one pressurized fluid inflow channel 70 and at least one pressurized fluid outflow channel 72. The inflow and outflow channels each communicate with the air cavity 54.

A pump 80 is connected in a fluid circuit with both the inflow and outflow channels 70, 72, respectively. The pump 80 is controlled by a pump controller 82. The controller 82 generates a pump control signal in accordance with the pressure values in the connection lines 110, 112 (FIG. 11) as monitored by the pressure sensors 114, 116.

The inflow and outflow channels 70, 72, respectively, are sized to pass a pressurized fluid through the air cavity 54 such that, in use, the spaced relationship between the partition and the window is maintained.

It should also be appreciated that in an alternative to this embodiment the window may be omitted and the lens of the spectrophotometer may effectively serve as the upper boundary of the cavity 54. In this event, a suitable expedient is provided to mount the photometer to the body of the flow cell.

The present invention may also be implemented in the form of a probe apparatus 150, as compared to the flow cell described earlier.

As shown in FIGS. 15A and 15B the probe 150 in accordance with this aspect of the present invention comprises a housing member 154 having a window 20 transparent to interrogating radiation mounted at a first end thereof. The housing 154 preferably takes the form of a generally elongated, tubular member. The cross section of the housing can assume any convenient configuration. The exterior of the housing is threaded over a portion of its length, as at 159, whereby the probe 150 may be mounted within the mounting openings 108A, 108B (FIG. 12). Other appropriate mounting arrangements may be used.

Interrogating radiation is conducted toward the window and reflected radiation exiting from the window by one or more fiber bundles 156A through 156D. (In the drawings the fiber 156D extends through the center of the housing 154 while the fibers 156A through 156C are arrayed about the interior of the housing. Other suitable arrangements may also be used.) Each fiber may be secured within the housing 154 by a suitable clamp 158. Alternative arrangements for conducting radiation to and from the window, such as interior mirrors, may be provided.

A partition 50 that is transparent to interrogating radiation is mounted at the end of the housing 154 in spaced relationship to the window 20. The partition 50 has a first surface and a second surface thereon. The first surface 50A of the partition confronts and cooperates with the window 20 to define a cavity therebetween 54. The spacing between the partition 50 and the window 20 is such that radiation reflected from a liquid disposed in contact with the second surface 50B of the partition is prevented from evanescently coupling into the window such that the reflected radiation undergoes total internal reflection in the partition 50 rather than in the window.

In use, with reference again to FIG. 12, the probe 150 may be mounted into the openings 108A and/or 108B (or at any other convenient locations within the flow path) using the external threads 159. As in the case of the flow cell, interrogating radiation from a suitable source is conducted toward the window. The incident radiation is conducted to a reflectance mode spectrophotometer.

EXAMPLE

The prevention in light disruption and the corresponding improvements in chroma and in color sensitivity afforded by a flow cell in accordance with the present invention may be understood from the following Example.

Sample 1 was an orange tint available from E.I. du Pont de Nemours and Co., Wilmington Del. as Tint 853J mixed with a suitable amount of white mixing base to give full spectral information. Sample 2 was the same orange tint doped with 0.32% of a desaturating black colorant available from E.I. du Pont de Nemours and Co., Wilmington Del. as Tint 806J.

Reflectance versus wavelength measurements for the two liquid samples Sample 1 and Sample 2 were made using each of three instruments, the Reference Instrument, the Prior Art Comparison Instrument, and the Invention Instrument.

The Reference Instrument was a rotating disc system generally as described in German Patent DE 25 25 701. Liquid Samples 1 and 2 were separately applied using a slotted container onto the surface of a rotating disc and free surface measurements of the reflectance were made. The reflectance measurements from this instrument were selected as the reference standard since they most closely present the color appearance of the sample as seen by the human eye. Wet free surface measurements approximate those available using a dry free surface measurement technique described in the Background portion of this application.

The Prior Art Comparison Instrument was a closed flow cell system generally as described in U.S. Pat. No. 4,511,251 (Falcoff et al.). Liquid Samples 1 and 2 were pumped through the flow cell. Owing to the construction of the cell each liquid sample was in intimate contact with the window of the cell as the sample passed therethrough.

The Invention Instrument was a closed flow cell having a partition in accordance with the present invention, substantially as described herein and as illustrated in FIGS. 2-7.

For each instrument reflectance values for each liquid sample were measured using a model MA90BR spectrophotometer available from X-Rite, Incorporated, Grandville, Mich.

CIELab76 values L, a, b for each set of measurements were calculated using the reflectance spectra. Chroma ($C^*_{ab}$) was calculated using CIELab76 formalism: ($C^*_{ab}=[a^{*2}+b^{*2}]^{1/2}$).

Changes $\Delta L$, $\Delta a$ and $\Delta b$ between the reflectance values measured for Samples 1 and 2 with each instrument were also calculated.

Figure 16:
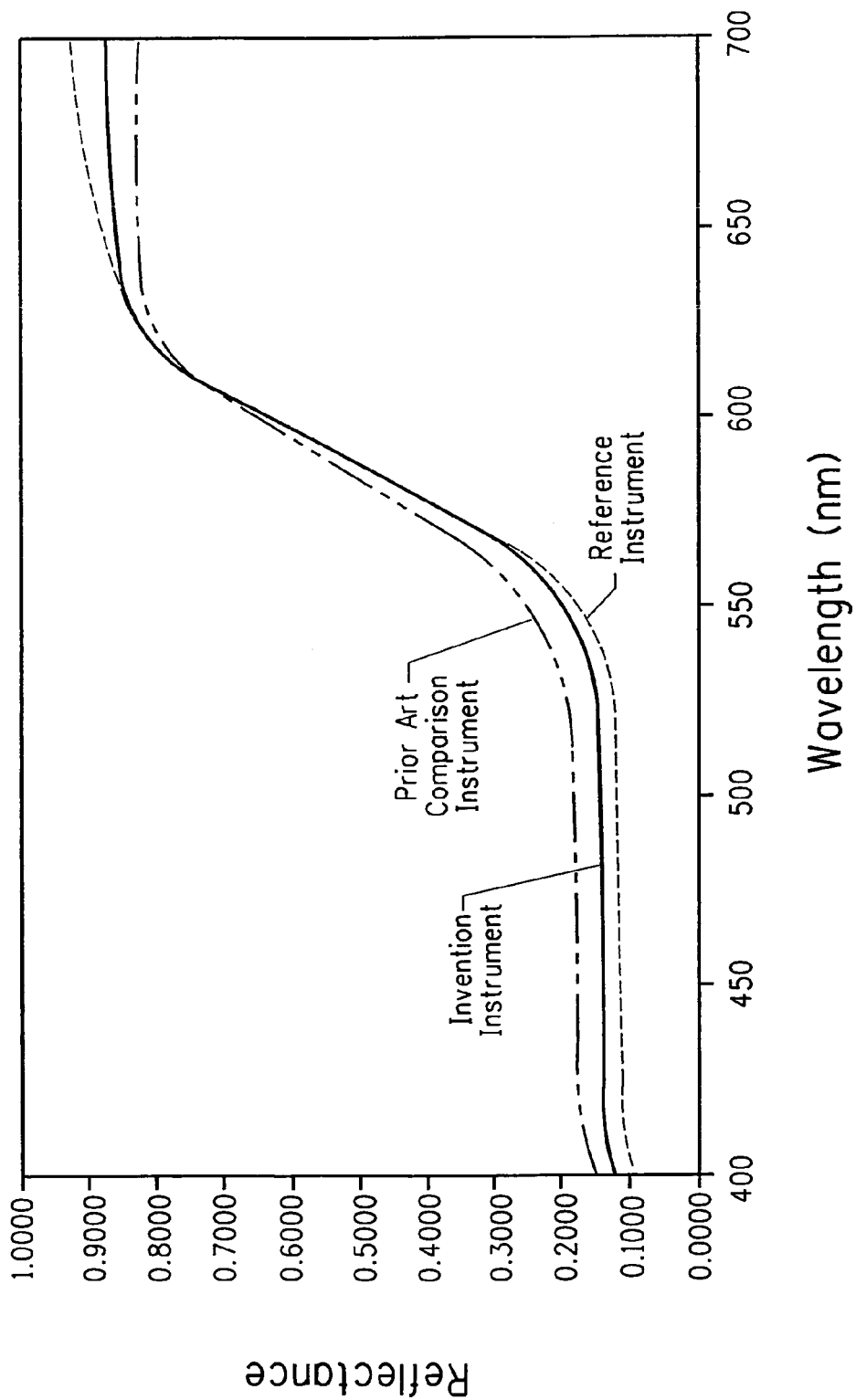
FIG. 16 is a plot of the reflectance versus wavelength for Example Sample 1 as measured with each instrument discussed in the Example.

All measured and calculated results are set forth in the following Table. A plot of the reflectance versus wavelength plot for Sample 1 as measured with each instrument is graphically illustrated in FIG. 16.

TABLE

| nm | Reference Instrument Sample 1 | Reference Instrument Sample 2 | Prior Art Comparison Instrument Sample 1 | Prior Art Comparison Instrument Sample 2 | Invention Instrument Sample 1 | Invention Instrument Sample 2 |
|---|---|---|---|---|---|---|
| 400 | 0.0953 | 0.0953 | 0.1504 | 0.1507 | 0.1239 | 0.1244 |
| 410 | 0.1059 | 0.1058 | 0.1662 | 0.1665 | 0.1330 | 0.1337 |
| 420 | 0.1094 | 0.1094 | 0.1719 | 0.1720 | 0.1354 | 0.1358 |
| 430 | 0.1112 | 0.1112 | 0.1738 | 0.1736 | 0.1363 | 0.1366 |
| 440 | 0.1123 | 0.1123 | 0.1744 | 0.1742 | 0.1366 | 0.1372 |
| 450 | 0.1122 | 0.1121 | 0.1749 | 0.1747 | 0.1361 | 0.1366 |
| 460 | 0.1119 | 0.1120 | 0.1733 | 0.1734 | 0.1351 | 0.1357 |
| 470 | 0.1121 | 0.1122 | 0.1726 | 0.1726 | 0.1346 | 0.1354 |
| 480 | 0.1126 | 0.1128 | 0.1734 | 0.1731 | 0.1347 | 0.1354 |
| 490 | 0.1143 | 0.1143 | 0.1750 | 0.1748 | 0.1355 | 0.1361 |
| 500 | 0.1169 | 0.1168 | 0.1773 | 0.1772 | 0.1375 | 0.1380 |
| 510 | 0.1208 | 0.1208 | 0.1816 | 0.1813 | 0.1412 | 0.1419 |
| 520 | 0.1282 | 0.1283 | 0.1905 | 0.1899 | 0.1478 | 0.1487 |
| 530 | 0.1406 | 0.1409 | 0.2046 | 0.2040 | 0.1596 | 0.1604 |
| 540 | 0.1586 | 0.1586 | 0.2232 | 0.2230 | 0.1760 | 0.1766 |
| 550 | 0.1852 | 0.1852 | 0.2520 | 0.2514 | 0.2004 | 0.2010 |
| 560 | 0.2301 | 0.2298 | 0.2990 | 0.2976 | 0.2417 | 0.2425 |
| 570 | 0.3013 | 0.3002 | 0.3693 | 0.3676 | 0.3078 | 0.3085 |
| 580 | 0.3971 | 0.3937 | 0.4579 | 0.4542 | 0.3991 | 0.3980 |
| 590 | 0.5135 | 0.5042 | 0.5593 | 0.5529 | 0.5155 | 0.5087 |
| 600 | 0.6307 | 0.6143 | 0.6543 | 0.6434 | 0.6377 | 0.6221 |
| 610 | 0.7301 | 0.7057 | 0.7335 | 0.7146 | 0.7410 | 0.7141 |
| 620 | 0.7977 | 0.7644 | 0.7853 | 0.7580 | 0.8049 | 0.7697 |
| 630 | 0.8390 | 0.7929 | 0.8093 | 0.7786 | 0.8364 | 0.7976 |
| 640 | 0.8645 | 0.8075 | 0.8178 | 0.7856 | 0.8510 | 0.8106 |
| 650 | 0.8797 | 0.8172 | 0.8227 | 0.7894 | 0.8584 | 0.8169 |
| 660 | 0.8908 | 0.8254 | 0.8260 | 0.7915 | 0.8626 | 0.8204 |
| 670 | 0.8989 | 0.8341 | 0.8287 | 0.7927 | 0.8649 | 0.8222 |
| 680 | 0.9065 | 0.8425 | 0.8308 | 0.7931 | 0.8667 | 0.8235 |
| 690 | 0.9160 | 0.8499 | 0.8319 | 0.7927 | 0.8695 | 0.8256 |
| 700 | 0.9273 | 0.8574 | 0.8325 | 0.7918 | 0.8731 | 0.8283 |
| L | 62.12 | 61.57 | 66.23 | 65.86 | 63.16 | 62.75 |
| a | 43.79 | 42.13 | 35.86 | 34.81 | 41.78 | 40.25 |
| b | 38.18 | 37.24 | 30.09 | 29.47 | 33.61 | 32.76 |
| Chr | 58.10 | 56.23 | 46.81 | 45.61 | 53.62 | 51.90 |
| ΔL |  | −0.55 |  | −0.37 |  | −0.41 |
| Δa |  | −1.66 |  | −1.05 |  | −1.52 |
| Δb |  | −0.95 |  | −0.62 |  | −0.85 |

Discussion In the blue region of the measurement spectrum (400-500 nm) the Prior Art Comparison Instrument shows elevated reflectance values as compared to both the Reference Instrument and the Invention Instrument. Conversely, in the red region of the measurement spectrum (600-700 nm) the values produced by the Prior Art Comparison Instrument were below those of both the Reference Instrument and the Invention Instrument. The increased reflectance baseline in the blue region and the decreased reflectance peak in the red region are believed attributable to the disruption and loss of light energy from the window, as discussed in the Background.

The chroma value for the Reference Instrument was 58.10, while the chroma value for the Prior Art Comparison Instrument was 46.81 and the chroma value for the Invention Instrument was 53.62. Referring to the Table, the difference between the chroma measured with the Prior Art Instrument and the reference instrument is 11.29. The difference between the chroma measured with the Invention Instrument and the Reference Instrument is 4.48. The improvement can be measured by taking the difference of the two differences, which is 6.81. Therefore the relative improvement is just 6.81/11.29, or ~60%. Thus, the Invention Instrument provided a significant improvement over the Prior Art Comparison Instrument.

A comparison of the changes Δa and Δb reveals that the Invention Instrument also provides significantly better color sensitivity as compared to the Prior Art Comparison Instrument.

The Reference Instrument recorded changes Δa and Δb between Sample 1 and Sample 2 of −1.66 and −0.95, respectively. The Prior Art Instrument recorded Δa of −1.05 and Δb of −0.62, while the Invention Instrument recorded Δa of −1.52 and Δb of −0.85. To determine the sensitivity of the Invention and Prior Art Instruments, it is only necessary to calculate the percentage of the total change recorded by the Reference Instrument by both the Prior Art Instrument and the Invention instrument. This can be done by forming the ratios of the Δa and Δb for each instrument with respect to the Reference Instrument. To wit,

| Δa | Prior Art Instrument | 1.05/1.66 = 63% |
|---|---|---|
|  | Invention Instrument | 1.52/1.66 = 91% |
| Δb | Prior Art Instrument | .62/.95 = 66% |
|  | Invention Instrument | .85/.95 = 89% |

For both Δa and Δb the Invention Instrument recorded approximately 90% of the sensitivity to color change of the free surface measurement, while the Prior Art Comparison Instrument exhibited under 63% and 66%% of the sensitivity, respectively.

From the foregoing it may be appreciated from the foregoing that the flow cell of the present invention provides significant advantages over prior art systems.

The present invention avoids the measurement problem presented when a window of the cell is in intimate contact with the liquid under test. By using a partition which is sufficiently thin to mitigate the disruption of light and attendant loss of chroma to confine the pressurized liquid sample, the present invention facilitates color measurement via reflectance spectroscopy of wet liquids in a closed system that produces acceptably consistent results and predicts with confidence that the wet readings will also match the standard in the dry.

The presence of the spacers or the pressurized fluid behind the partition provides sufficient strength to prevent bowing which may occur when the sample is under pressure. Thus, the present invention solves the seemingly contradictory problem of strength (thickness) versus chroma loss that attends the use of a windowed system.

By providing the coatings of fluoropolymer material the cell is able to be cleaned rapidly [within one to two (1 or 2) minutes] so that the cycle time of the measurement is extremely small compared to process changes.

Because the flow cell embodiment or the probe embodiment of the present invention can be interposed in the flow path of a pressurized liquid, delivery of a sample under test can be accomplished quickly and easily. This permits measurements of color can be made rapidly;

Moreover, because the flow cell or probe can operate within the confines of a closed system, the cell and probe may be placed on a plant floor in an environment that may contain an explosive atmosphere.

Those skilled in the art, having the benefit of the teachings of the present invention as hereinabove set forth may effect numerous modifications thereto. Such modifications are to be construed as lying within the contemplation of the present invention as defined by the appended claims.

What is claimed is:

1. A flow cell for measuring a property of a pressurized flowing fluid using interrogating radiation at a predetermined wavelength, the flow cell comprising:
   a first and a second housing member, one of the housing members having a window transparent to interrogating radiation;
   a partition transparent to interrogating radiation mounted within the flow cell in spaced relationship to both the housing member having the window and to the other housing member,
   the partition having a first surface and a second surface thereon, the first surface of the partition confronting the window in the one housing member and the second surface of the partition confronting the other housing member,
   the partition being disposed such that the first surface of the partition and the window cooperate to define a cavity therebetween while the second surface of the partition and the other housing member cooperate to define a fluid sample chamber therebetween,
   the spaced relationship between the partition and the window being such that radiation reflected from a fluid in the sample chamber is able to undergo total internal reflection in the partition without evanescently coupling into the window; and
   an inflow and an outflow channel formed in the housing member having the window, the inflow and outflow channels each communicating with the cavity, the inflow and outflow channels being sized to pass a pressurized fluid through the cavity such that, in use, the spaced relationship between the partition and the window is maintained by a pressurized fluid in the cavity.

2. The flow cell of claim 1 wherein the first surface of the partition is spaced from the window by a distance not less than three (3) times the predetermined wavelength of the interrogating radiation.

3. The flow cell of claim 1 wherein the partition is a substantially planar member having a maximum thickness, the maximum thickness being such that propagation of radiation due to total internal reflection within the partition is minimized,
   whereby that substantially all of the radiation reflected from the fluid being measured exits the partition within a predetermined lateral distance along the plane of the partition.

4. The flow cell of claim 3 wherein the partition has a maximum thickness in the range from 0.005 to 0.010 inches.

5. The flow cell of claim 1 wherein the partition has a maximum thickness in the range from 0.005 to 0.010 inches.

6. The flow cell of claim 1 wherein the partition is a flexible polymer membrane.

7. The flow cell of claim 1 wherein the other housing member has a supply passage and a removal passage formed therein, the supply passage and the removal passage each communicating with the sample chamber,
   the supply passage, the sample chamber and the removal passage cooperating to define a flow path through the flow cell,
   the supply passage, the sample chamber and the removal passage each being configured such that any cross section taken in a plane substantially perpendicular to the flow path at any location therealong exhibits substantially the same cross-sectional area.

8. The flow cell of claim 7
   further comprising:
   a pressure sensor for monitoring the pressure of a fluid supplied to the supply passage; and
   a controller for generating a pump control signal to control the pressure of the pressurized fluid in the cavity in accordance with the pressure value monitored by the pressure sensor.

9. The flow cell of claim 7 wherein the housing member has a supply passage and a removal passage formed therein, the supply passage and the removal passage each communicating with the sample chamber,
   the flow cell further comprising:
   a first pressure sensor for monitoring the pressure of a fluid supplied to the supply passage;
   a second pressure sensor for monitoring the pressure of a fluid present in the removal passage; and
   a controller for generating a pump control signal to control the pressure of the pressurized fluid in the cavity in accordance with the pressure value monitored by the first and second pressure sensors.

10. The flow cell of claim 1 wherein the housing member has a supply passage and a removal passage formed therein, the supply passage and the removal passage each communicating with the sample chamber,
    the flow cell further comprising:
    a pressure sensor for monitoring the pressure of a fluid present in the removal passage; and
    a controller for generating a pump control signal to control the pressure of the pressurized fluid in the cavity in accordance with the pressure value monitored by the pressure sensor.

* * * * *